(12) United States Patent
Lim et al.

(10) Patent No.: US 11,925,586 B2
(45) Date of Patent: Mar. 12, 2024

(54) SURGICAL PLATFORM AND TROLLEY ASSEMBLY

(71) Applicant: Mazor Robotics Ltd., Caesarea (IL)

(72) Inventors: Roy K. Lim, Memphis, TN (US); Arik A. Levy, Caesarea (IL); Katharine E. Darling, Louisville, CO (US); Mark C. Dace, Memphis, TN (US); Yonatan Ushpizin, Caesarea (IL)

(73) Assignee: MAZOR ROBOTICS LTD., Caesarea (IL)

( * ) Notice: Subject to any disclaimer, the term of this patent is extended or adjusted under 35 U.S.C. 154(b) by 147 days.

(21) Appl. No.: 17/704,759

(22) Filed: Mar. 25, 2022

(65) Prior Publication Data

US 2023/0301862 A1 Sep. 28, 2023

(51) Int. Cl.
*A61G 13/10* (2006.01)
*A61B 34/30* (2016.01)
*A61G 13/06* (2006.01)
*B25J 5/00* (2006.01)

(52) U.S. Cl.
CPC .......... *A61G 13/104* (2013.01); *A61G 13/06* (2013.01); *B25J 5/007* (2013.01); *A61B 34/30* (2016.02)

(58) Field of Classification Search
USPC ............................................................ 5/145
See application file for complete search history.

(56) References Cited

U.S. PATENT DOCUMENTS

| | | |
|---|---|---|
| 2,691,979 A | 10/1954 | Watson |
| 3,060,925 A | 10/1962 | Honsaker et al. |
| 3,227,440 A | 1/1966 | Scott |
| 3,293,667 A | 12/1966 | Ohrberg |
| 3,306,287 A | 2/1967 | Arp |
| 3,389,702 A | 6/1968 | Kennedy |
| 3,828,377 A | 8/1974 | Fary, Sr. |
| 4,029,089 A | 6/1977 | Mulhlland |
| 4,194,257 A | 3/1980 | Martin et al. |
| 4,627,119 A | 12/1986 | Hachey et al. |
| 4,655,200 A | 4/1987 | Knight |
| 4,705,026 A | 11/1987 | Chaussy |
| 4,866,796 A | 9/1989 | Robinson |
| 4,872,656 A | 10/1989 | Brendgord |
| 4,901,384 A | 2/1990 | Eary |
| 4,915,101 A | 4/1990 | Cuccia |
| 5,009,407 A | 4/1991 | Watanabe |
| 5,088,706 A | 2/1992 | Jackson |
| 5,103,511 A | 4/1992 | Sequin |

(Continued)

OTHER PUBLICATIONS

International Search Report and Written Opinion dated Jun. 27, 2023 from International Application No. PCT/IL2023/050291.

(Continued)

*Primary Examiner* — Justin C Mikowski
*Assistant Examiner* — Adam C Ortiz

(57) ABSTRACT

A surgical platform and trolley assembly and an interface of a robotic system are provided. The surgical platform and trolley assembly includes a trolley portion and a surgical platform portion. The trolley portion supports the surgical platform portion, and affords positioning and repositioning of the surgical platform portion relative to the interface of the robotic system. An end portion of the surgical platform portion is attachable relative to the robotic system via engagement to the interface.

20 Claims, 19 Drawing Sheets

(56) References Cited

U.S. PATENT DOCUMENTS

| | | | |
|---|---|---|---|
| 5,131,106 A | 7/1992 | Jackson | |
| 5,362,302 A | 11/1994 | Jenson et al. | |
| 5,390,383 A | 2/1995 | Carn | |
| 5,410,769 A | 5/1995 | Waterman | |
| 5,444,882 A | 8/1995 | Andrews | |
| 5,564,662 A * | 10/1996 | Lussi | F16M 7/00 |
| | | | 5/310 |
| 5,613,254 A | 3/1997 | Clayman | |
| 5,642,302 A | 6/1997 | Dumont | |
| 5,860,899 A | 1/1999 | Rassman | |
| 5,991,651 A | 11/1999 | LaBarbera | |
| 6,003,176 A | 12/1999 | Wasley | |
| 6,076,525 A | 6/2000 | Hoffman | |
| 6,112,349 A | 9/2000 | Connolly | |
| 6,154,901 A | 12/2000 | Carr | |
| 6,260,220 B1 | 7/2001 | Lamb | |
| 6,295,671 B1 | 10/2001 | Reesby et al. | |
| 6,311,349 B1 | 11/2001 | Kazakia | |
| 6,367,104 B1 | 4/2002 | Fallbo, Sr. et al. | |
| 6,378,149 B1 | 4/2002 | Sanders et al. | |
| 6,516,483 B1 | 2/2003 | VanSteenburg | |
| 6,566,833 B2 | 5/2003 | Barlett | |
| 6,615,430 B2 | 9/2003 | Heimbrock | |
| 6,671,905 B2 | 1/2004 | Bartlett et al. | |
| 6,681,423 B2 * | 1/2004 | Zachrisson | A61G 13/04 |
| | | | 5/601 |
| 6,701,553 B1 | 3/2004 | Hand et al. | |
| 6,701,554 B2 | 3/2004 | Heimbrock | |
| 6,701,558 B2 | 3/2004 | VanSteenburg | |
| 6,715,169 B2 | 4/2004 | Niederkrom | |
| 6,728,983 B2 | 5/2004 | Bartlett et al. | |
| 6,732,390 B2 | 5/2004 | Krywiczanin | |
| 6,739,006 B2 | 5/2004 | Borders et al. | |
| 6,820,621 B2 | 11/2004 | DeMayo | |
| 6,874,181 B1 | 4/2005 | Connolly et al. | |
| 6,934,986 B2 | 8/2005 | Krywiczanin et al. | |
| 6,941,951 B2 | 9/2005 | Hubert et al. | |
| 6,966,081 B1 | 11/2005 | Sharps | |
| 7,100,225 B1 | 9/2006 | Bailey | |
| 7,152,261 B2 | 12/2006 | Jackson | |
| 7,189,214 B1 | 3/2007 | Saunders | |
| 7,219,379 B2 | 5/2007 | Krywiczanin et al. | |
| 7,234,180 B2 | 6/2007 | Horton et al. | |
| 7,290,302 B2 | 11/2007 | Sharps | |
| 7,343,635 B2 | 3/2008 | Jackson | |
| 7,426,930 B2 | 9/2008 | Bailey | |
| 7,472,440 B2 | 1/2009 | Bartlett et al. | |
| 7,484,253 B1 | 2/2009 | Coppens | |
| 7,496,980 B2 | 3/2009 | Sharps | |
| 7,565,708 B2 | 7/2009 | Jackson | |
| 7,600,281 B2 | 10/2009 | Skripps | |
| 7,669,262 B2 | 3/2010 | Skripps | |
| 7,739,762 B2 | 6/2010 | Lamb et al. | |
| 7,882,583 B2 | 2/2011 | Skripps | |
| 8,060,960 B2 | 11/2011 | Jackson | |
| 8,118,029 B2 | 2/2012 | Gneiting et al. | |
| 8,286,283 B2 | 10/2012 | Copeland et al. | |
| 8,286,637 B2 | 10/2012 | Kaska | |
| 8,381,335 B2 | 2/2013 | Ahlman | |
| 8,413,660 B2 | 4/2013 | Weinstein et al. | |
| 8,424,133 B1 * | 4/2013 | Rossi | A61G 13/04 |
| | | | 5/607 |
| 8,439,948 B1 | 5/2013 | King | |
| 8,443,473 B2 | 5/2013 | Maxwell | |
| 8,584,281 B2 | 11/2013 | Diel et al. | |
| 8,635,725 B2 | 1/2014 | Tannoury et al. | |
| 8,677,529 B2 | 3/2014 | Jackson | |
| 8,707,484 B2 | 4/2014 | Jackson et al. | |
| 8,978,180 B2 | 3/2015 | Jackson | |
| 9,072,646 B2 | 7/2015 | Skripps et al. | |
| 9,180,062 B2 | 11/2015 | Jackson | |
| 9,186,291 B2 | 11/2015 | Jackson et al. | |
| 9,226,865 B2 | 1/2016 | Jackson et al. | |
| 9,265,680 B2 | 2/2016 | Sharps | |
| 9,295,433 B2 | 3/2016 | Jackson et al. | |
| 9,308,145 B2 | 4/2016 | Jackson | |
| 9,339,430 B2 | 5/2016 | Jackson et al. | |
| 9,358,170 B2 | 6/2016 | Jackson | |
| 9,402,775 B2 | 8/2016 | Jackson et al. | |
| 9,414,982 B2 | 8/2016 | Jackson | |
| 9,468,576 B2 | 10/2016 | Jackson | |
| 9,498,397 B2 | 11/2016 | Hight et al. | |
| 9,522,078 B2 | 12/2016 | Pizzini | |
| 9,554,959 B2 | 1/2017 | Carn | |
| 9,622,928 B2 | 4/2017 | Jackson et al. | |
| 9,655,793 B2 | 5/2017 | Hertz | |
| 9,700,476 B2 | 7/2017 | Hoel et al. | |
| 9,713,562 B2 | 7/2017 | Perlman et al. | |
| 9,744,089 B2 | 8/2017 | Jackson | |
| 9,849,054 B2 | 12/2017 | Jackson | |
| 9,937,006 B2 | 4/2018 | Skripps et al. | |
| 9,993,380 B2 | 6/2018 | Jackson | |
| 10,136,863 B2 | 11/2018 | Kaiser et al. | |
| 10,314,758 B2 | 6/2019 | Dolliver et al. | |
| 10,342,722 B2 | 7/2019 | Garrido | |
| RE47,588 E * | 9/2019 | Erbel | A61B 6/0421 |
| 10,406,054 B1 | 9/2019 | Scholl et al. | |
| 10,426,684 B2 | 10/2019 | Dubois et al. | |
| 10,531,998 B2 | 1/2020 | Jackson et al. | |
| 10,543,142 B2 | 1/2020 | Lim et al. | |
| 10,548,796 B2 | 2/2020 | Lim et al. | |
| 10,576,006 B2 | 3/2020 | Lim et al. | |
| 10,695,252 B2 | 6/2020 | Jackson | |
| 10,722,413 B2 | 7/2020 | Lim et al. | |
| 10,729,607 B2 | 8/2020 | Jackson | |
| 10,751,240 B2 | 8/2020 | Lim et al. | |
| 10,835,438 B2 | 11/2020 | Jackson | |
| 10,835,439 B2 | 11/2020 | Lim et al. | |
| 10,849,809 B2 | 12/2020 | Lim et al. | |
| 10,874,570 B2 | 12/2020 | Lim et al. | |
| 10,881,570 B2 | 1/2021 | Lim et al. | |
| 10,888,484 B2 | 1/2021 | Lim et al. | |
| 10,893,996 B2 | 1/2021 | Lim et al. | |
| 10,898,401 B2 | 1/2021 | Lim et al. | |
| 10,900,448 B2 | 1/2021 | Lim et al. | |
| 2002/0138905 A1 | 10/2002 | Barltett et al. | |
| 2002/0138906 A1 | 10/2002 | Barltett et al. | |
| 2002/0157186 A1 | 10/2002 | VanSteenburg | |
| 2003/0140419 A1 | 7/2003 | Barltett et al. | |
| 2003/0140420 A1 | 7/2003 | Niederkrom | |
| 2003/0145382 A1 | 8/2003 | Krywiczanin | |
| 2003/0178027 A1 | 9/2003 | DeMayo et al. | |
| 2004/0010849 A1 | 1/2004 | Krywiczanin et al. | |
| 2004/0133979 A1 | 7/2004 | Newkirk et al. | |
| 2004/0133983 A1 | 7/2004 | Newkirk | |
| 2005/0015878 A1 * | 1/2005 | Bannister | A61G 13/06 |
| | | | 5/618 |
| 2005/0181917 A1 | 8/2005 | Dayal | |
| 2006/0037141 A1 | 2/2006 | Krywiczanin et al. | |
| 2006/0123546 A1 | 6/2006 | Horton | |
| 2006/0162076 A1 | 7/2006 | Bartlett et al. | |
| 2006/0162084 A1 | 7/2006 | Mezue | |
| 2006/0185090 A1 | 8/2006 | Jackson | |
| 2007/0107125 A1 * | 5/2007 | Koch | A61G 13/04 |
| | | | 5/618 |
| 2008/0034502 A1 | 2/2008 | Copeland et al. | |
| 2008/0134434 A1 | 6/2008 | Celauro | |
| 2008/0222811 A1 | 9/2008 | Gilbert et al. | |
| 2009/0139030 A1 | 6/2009 | Yang | |
| 2010/0037397 A1 | 2/2010 | Wood | |
| 2010/0192300 A1 | 8/2010 | Tannoury | |
| 2010/0293719 A1 | 11/2010 | Klemm et al. | |
| 2011/0099716 A1 | 5/2011 | Jackson | |
| 2012/0103344 A1 | 5/2012 | Hunter | |
| 2012/0144589 A1 | 6/2012 | Skripps et al. | |
| 2012/0255122 A1 | 10/2012 | Diel et al. | |
| 2013/0111666 A1 | 5/2013 | Jackson | |
| 2013/0191994 A1 | 8/2013 | Bellows et al. | |
| 2013/0283526 A1 | 10/2013 | Gagliardi | |
| 2013/0307298 A1 | 11/2013 | Meiki | |
| 2014/0020183 A1 | 1/2014 | Dominick | |
| 2014/0059773 A1 | 3/2014 | Carn | |
| 2014/0068861 A1 | 3/2014 | Jackson | |
| 2014/0109316 A1 | 4/2014 | Jackson et al. | |

(56) References Cited

U.S. PATENT DOCUMENTS

| | | |
|---|---|---|
| 2014/0137327 A1 | 5/2014 | Tannoury et al. |
| 2015/0044956 A1 | 2/2015 | Hacker |
| 2015/0245971 A1 | 9/2015 | Bernardoni et al. |
| 2015/0272681 A1 | 10/2015 | Skripps et al. |
| 2016/0000621 A1 | 1/2016 | Jackson |
| 2016/0081582 A1* | 3/2016 | Rapoport ............... G01R 33/30 600/415 |
| 2016/0089287 A1 | 3/2016 | Buerstner |
| 2016/0193099 A1 | 7/2016 | Drake |
| 2017/0027797 A1 | 2/2017 | Dolliver et al. |
| 2017/0049651 A1 | 2/2017 | Lim |
| 2017/0049653 A1 | 2/2017 | Lim |
| 2017/0079864 A1 | 3/2017 | Riley |
| 2017/0112698 A1 | 4/2017 | Hight et al. |
| 2017/0135891 A1 | 5/2017 | Kettner |
| 2017/0151115 A1 | 6/2017 | Jackson |
| 2017/0341232 A1 | 11/2017 | Perplies |
| 2017/0348171 A1 | 12/2017 | Jackson |
| 2018/0116891 A1 | 5/2018 | Beale et al. |
| 2018/0185228 A1 | 7/2018 | Catacchio et al. |
| 2018/0193104 A1 | 7/2018 | Beale et al. |
| 2018/0363596 A1 | 12/2018 | Lim et al. |
| 2019/0000702 A1 | 1/2019 | Lim et al. |
| 2019/0000707 A1 | 1/2019 | Lim et al. |
| 2019/0046381 A1 | 2/2019 | Lim et al. |
| 2019/0046383 A1 | 2/2019 | Lim et al. |
| 2019/0209409 A1 | 7/2019 | Jackson et al. |
| 2020/0000668 A1 | 1/2020 | Lim et al. |
| 2020/0060913 A1 | 2/2020 | Lim et al. |
| 2020/0060914 A1 | 2/2020 | Lim et al. |
| 2020/0060915 A1 | 2/2020 | Lim et al. |
| 2020/0138660 A1 | 5/2020 | Jackson |
| 2020/0170868 A1 | 6/2020 | Jackson |
| 2020/0188208 A1 | 6/2020 | Lim et al. |
| 2020/0138659 A1 | 7/2020 | Lim et al. |
| 2020/0281788 A1 | 9/2020 | Lim et al. |
| 2020/0297568 A1 | 9/2020 | Lim et al. |
| 2020/0337923 A1 | 10/2020 | Lim et al. |
| 2020/0337926 A1 | 10/2020 | Lim et al. |
| 2020/0337927 A1 | 10/2020 | Lim et al. |
| 2020/0360214 A1 | 11/2020 | Lim et al. |
| 2022/0008016 A1* | 1/2022 | Harrison ................ A61G 99/00 |

OTHER PUBLICATIONS

International Search Report and Written Opinion dated Jul. 19, 2023 in PCT/IB2023/054288.
International Search Report and Written Opinion dated Jul. 20, 2023 in PCT/IB2023/054218.

* cited by examiner

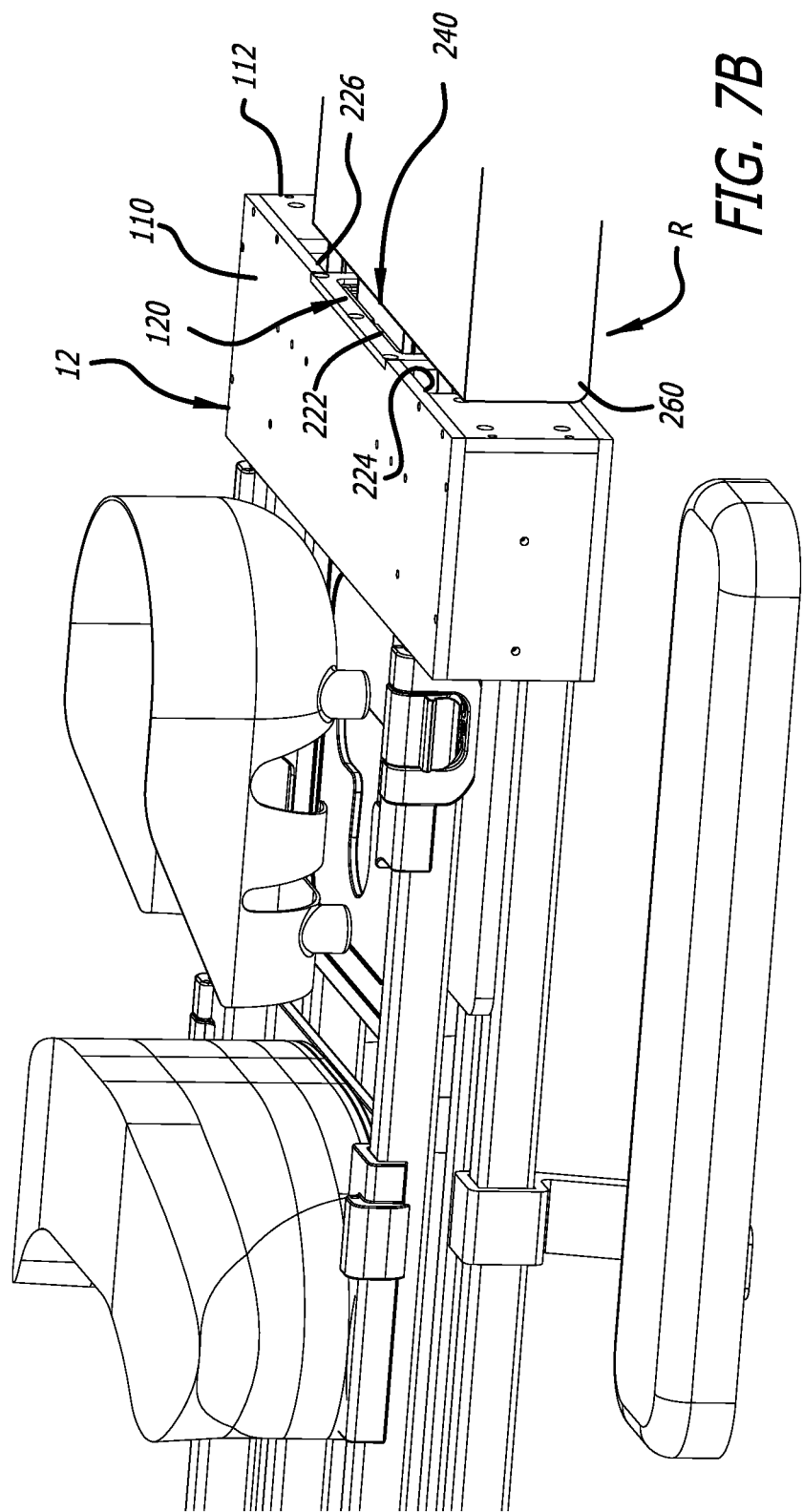

SURGICAL PLATFORM AND TROLLEY ASSEMBLY

FIELD

The present technology generally relates to a surgical platform and trolley assembly that can be used in performing conventional surgery on a patient supported thereby and/or can being interconnected relative to a surgical robot or robotic system that can be used to perform surgery on the patient.

BACKGROUND

Use of conventional surgical robots and robotic systems during surgery has become common. Such conventional surgical robots and robotic systems are typically separate from conventional surgical tables supporting patients, and the base portions thereof are typically positionable adjacent the heads, the feet, or the lateral sides of the patients and corresponding portions of the surgical tables. Movement of the conventional surgical robots and robotic systems is typically independent of and not coordinated with movement of the conventional surgical tables. To illustrate, the base portions of the conventional surgical robots and robotic systems typically can be positioned and repositioned on the ground relative to the surgical tables and the patients supported thereby, and various arms of the surgical robots and robotic systems typically can be positioned and repositioned to the surgical tables and the patients supported thereby. And the surgical tables typically can be positioned and repositioned on the ground relative to the surgical robot and robotic systems, and the conventional surgical tables typically can be adjusted/articulated to adjust/articulate the positions of the patients supported thereby. However, the conventional surgical robots and robotic systems do not control movement of the conventional surgical tables, and vice versa. As such, coordinated movement between the conventional surgical robots and robotics systems and the conventional surgical tables can be very difficult. Therefore, there is a need for a surgical table for use with a surgical robot or robotic system that can be interconnected relative to the surgical robot or robotic system to facilitate coordinated movement therebetween. Such a surgical table can itself be used to facilitate performance of conventional surgery on a patient supported thereby, and also can include a surgical platform portion that can be interconnected relative to the surgical robot or robotic system, and a trolley portion that can be used in positioning and repositioning the surgical platform to facilitate interconnection of the surgical platform relative to and surgery by the interconnected surgical robot or robotic system.

SUMMARY

The techniques of this disclosure generally relate to a surgical platform and trolley assembly that can be used as a surgical table for performing conventional surgery on a patient supported thereby, with portions thereof being interconnectable relative to a surgical robot or robotic system and other portions thereof being used to position and reposition the interconnectable portions relative to the surgical robot or robotic system to facilitate performance of the surgery by the interconnected surgical robot or robotic system.

In one aspect, the present disclosure provides a surgical platform and trolley assembly and an interface of a robotic system, the surgical platform and trolley assembly including a trolley portion including a support structure, a lifting/adjustment portion, and a carriage portion, the support structure having a first end, an opposite second end, a first end portion at the first end, a second end portion at the second end, and at least one cross member extending between the first end portion and the second end portion, the lifting/adjustment portion having a height that can be expanded and contracted relative to the support structure between a fully-contracted position and a fully-expanded position, and the lifting/adjustment portion being supported by the structure at and adjacent the second end thereof, and the carriage portion including at least one of a first side portion, a second side portion, an end portion, and a first portion of a connector attached to or received in the at least one of the first side portion, the second side portion, and the end portion, and being moveable upwardly via expansion of the lifting/adjustment portion and downwardly relative to the support structure via contraction of the lifting/adjustment portion, and the carriage portion being supported by the lifting/adjustment portion, and a surgical platform portion including a first end, an opposite second end, a first end portion at the first end, a second end portion at the second end, at least a first rail and a second rail extending between the first end portion and the second end portion, a head support, a chest support, and at least a first thigh support and a second thigh support supported between the at least a first rail and a second rail, and a second portion of the connector attached to or received in at least one of the second end portion and the at least a first rail and a second rail, the surgical platform portion being supportable at and adjacent the second end thereof by the lifting/adjustment portion, and connectable relative to the carriage portion via engagement of the first and second portions of the connector, the first end portion including a primary aperture and at least one secondary aperture provided to receive portions of the interface of the robotic system; and the interface of the robotic system including a tongue portion and at least one catch portion, the tongue portion being receivable in the primary aperture, and the at least one catch portion being receivable in the at least one secondary aperture to interconnect the surgical platform portion relative to the robotic system; where, when the surgical platform portion is supported by and connected to the carriage portion, the trolley portion can be positioned and repositioned relative to the robotic system to position the first end portion of the surgical platform portion adjacent the interface of the robotic system so that the tongue portion is received in the primary aperture and the at least one catch portion is received in the at least one secondary aperture to interconnect the surgical platform portion relative to the robotic system; and where, when the surgical platform portion is interconnected relative to the robotic system, the surgical platform portion can be disconnected from the carriage portion via disengagement of the first and second portions of the connector, and the trolley portion can be removed from adjacent the robotic system.

In another aspect, the present disclosure provides surgical platform and trolley assembly and an interface of a robotic system, the surgical platform and trolley assembly including a trolley portion including a support structure, and a carriage portion supporting a surgical platform above the support structure, the carriage portion including at least one of a first side portion, a second side portion, an end portion, and a first portion of a connector attached to or received in the at least one of the first side portion, the second side portion, and the end portion, and a surgical platform portion including a first end, an opposite second end, a first end portion at the first end, a second end portion at the second end, at least a first rail and a second rail extending between the first end portion and the second end portion, a head support, a chest support, and at least a first thigh support and a second thigh support supported between the at least a first rail and a second rail, and a second portion of the connector attached to or received in at least one of the second end portion and the at least a first rail and a second rail, the surgical platform portion connectable relative to the carriage portion via engagement of the first and second portions of the connector, the first end portion including a primary aperture and at least one secondary aperture provided to receive portions of the interface of the robotic system; and the interface of the robotic system including a tongue portion and at least one catch portion, the tongue portion being receivable in the primary aperture, and the at least one catch portion being receivable in the at least one secondary aperture to interconnect the surgical platform portion relative to the robotic system; where, when the surgical platform portion is supported by and connected to the carriage portion, the trolley portion can be positioned and repositioned relative to the robotic system to position the first end portion of the surgical platform portion adjacent the interface of the robotic system so that the tongue portion is received in the primary aperture and the at least one catch portion is received in the at least one secondary aperture to interconnect the surgical platform portion relative to the robotic system; and where, when the surgical platform portion is interconnected relative to the robotic system, the surgical platform portion can be disconnected from the carriage portion via disengagement of the first and second portions of the connector, and the trolley portion can be removed from adjacent the robotic system.

In yet another aspect, the present disclosure provides a surgical platform and trolley assembly and an interface of a robotic system, the surgical platform and trolley assembly including a trolley portion including a support structure, a lifting/adjustment portion, and a carriage portion, the support structure having a first end, an opposite second end, a first end portion at the first end, a second end portion at the second end, and at least one cross member extending between the first end portion and the second end portion, the lifting/adjustment portion having a height that can be expanded and contracted relative to the support structure between a fully-contracted position and a fully-expanded position, and the lifting/adjustment portion being supported by the structure at and adjacent the second end thereof, and the carriage portion including at least one of a first side portion, a second side portion, an end portion, and a first portion of a connector attached to or received in the at least one of the first side portion, the second side portion, and the end portion, and being moveable upwardly via expansion of the lifting/adjustment portion and downwardly relative to the support structure via contraction of the lifting/adjustment portion, and the carriage portion being supported by the lifting/adjustment portion, a surgical platform portion including a first end, an opposite second end, a first end portion at the first end, a second end portion at the second end, at least a first rail and a second rail extending between the first end portion and the second end portion, a head support, a chest support, and at least a first thigh support and a second thigh support supported between the at least a first rail and a second rail, and a second portion of the connector attached to or received in at least one of the second end portion and the at least a first rail and a second rail, the surgical platform portion being supportable at and adjacent the second end thereof by the lifting/adjustment portion, and connectable relative to the carriage portion via engagement of the first and second portions of the connector, the first end portion including a primary aperture and at least one secondary aperture provided to receive portions of the interface of the robotic system; and at least one controller provided controlling operation of at least portions of the surgical platform and trolley assembly and the robotic system, the controller being configured to control operation of the lifting/adjustment portion to position the first end portion of the surgical platform portion adjacent the interface of the robotic system; and the interface of the robotic system including a tongue portion and at least one catch portion, the tongue portion being receivable in the primary aperture, and the at least one catch portion being receivable in the at least one secondary aperture to interconnect the surgical platform portion relative to the robotic system; where, when the surgical platform portion is supported by and connected to the carriage portion, the trolley portion can be positioned and repositioned relative to the robotic system to position the first end portion of the surgical platform portion adjacent the interface of the robotic system so that the tongue portion is received in the primary aperture and the at least one catch portion is received in the at least one secondary aperture to interconnect the surgical platform portion relative to the robotic system; and where, when the surgical platform portion is interconnected relative to the robotic system, the surgical platform portion can be disconnected from the carriage portion via disengagement of the first and second portions of the connector, and the trolley portion can be removed from adjacent the robotic system.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The techniques of this disclosure generally relate to a surgical platform and trolley assembly.

FIG. 7B is a side, perspective view that illustrates the platform portion of the surgical platform and trolley assembly of FIG. 1 interconnected with the representation of the surgical robotic system or robotic surgical guidance system via attachment of the complimentary portions;

DETAILED DESCRIPTION

A preferred embodiment of a surgical table in the form of a surgical platform and trolley assembly of the present disclosure is generally indicated by the numeral 10 in FIGS. 1-4. The surgical platform and trolley assembly 10 includes a first end $E_1$, a second end $E_2$, and a mid-longitudinal axis $L_1$ extending through the first end $E_1$ and the second end $E_2$. As its name suggests, the surgical platform and trolley assembly 10 includes a surgical platform portion 12 and a trolley portion 14.

As depicted in FIGS. 1-4, the trolley portion 14 supports the surgical platform portion 12, and the surgical platform portion 12 can support a patient P thereon, as shown in FIGS. 9-15 and 17. Furthermore, the surgical platform and trolley assembly 10 can be used in performing surgery on the patient P positioned on the surgical platform portion 12, and/or the surgical platform and trolley assembly 10 can be positioned and repositioned relative to and can be used in association with a surgical robotic system or robotic surgical guidance system (hereinafter referred to as "robotic system") generally indicated by the letter R in FIGS. 6, 11-15, and 17. During use, the trolley portion 14 can be used to facilitate movement of the surgical platform portion 12 and can be used in orienting and reorienting the surgical platform portion 12 relative to the robotic system R. After being properly positioned relative to the robotic system R, the surgical platform portion 12 can be interconnected with the robotic system R and disconnected from the trolley portion 14. The robotic system R can be used for performing surgery or facilitating performance of surgery, and such surgery, for example, can include spinal surgery on the spine of the patient P.

As discussed below, the surgical platform and trolley assembly 10 and/or the robotic system R can include a controller or controllers for controlling one or more actuators included in the surgical platform and trolley assembly 10 and/or the robotic system R to facilitate the operation thereof. In some embodiments, for example, such controlled automation of the surgical platform and trolley assembly 10 and the robotic system R can coordinate movement therebetween.

Figure 1:
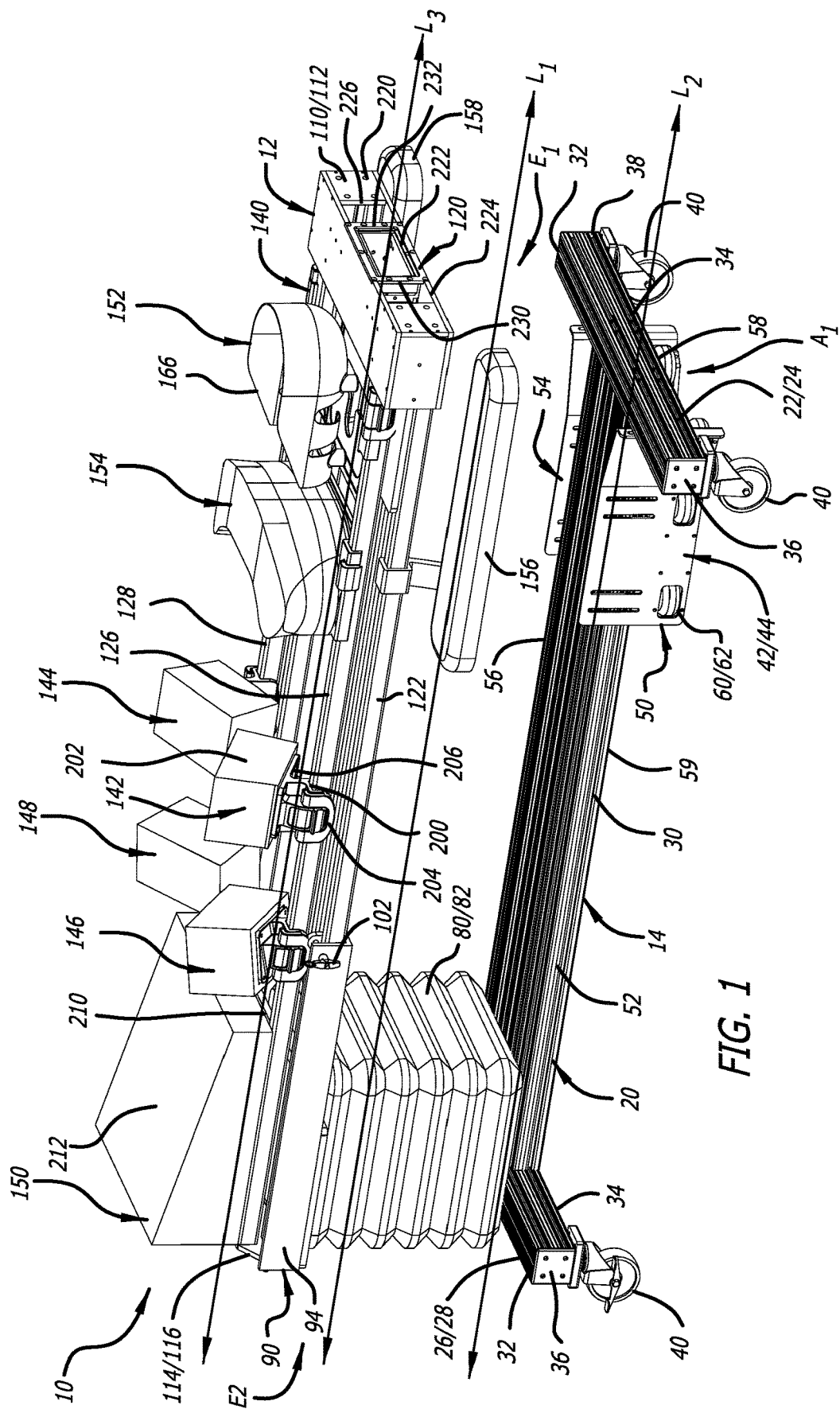
FIG. 1 is a side, perspective view that illustrates a surgical platform and trolley assembly of the present disclosure that includes a platform portion and a trolley portion supporting the platform portion.
Figure 2:
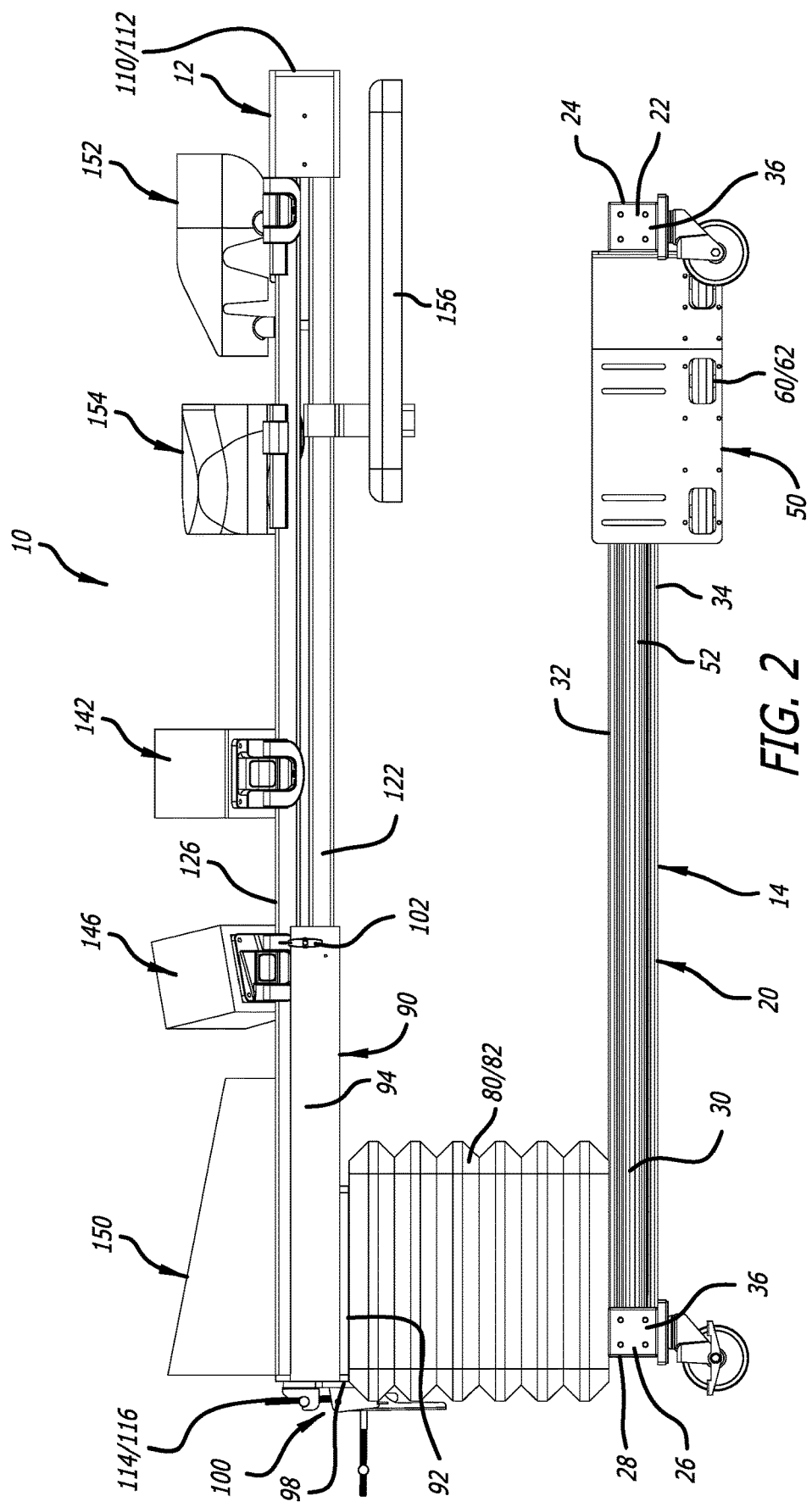
FIG. 2 is a first side, elevational view that illustrates the surgical platform and trolley assembly of FIG. 1.
Figure 3:
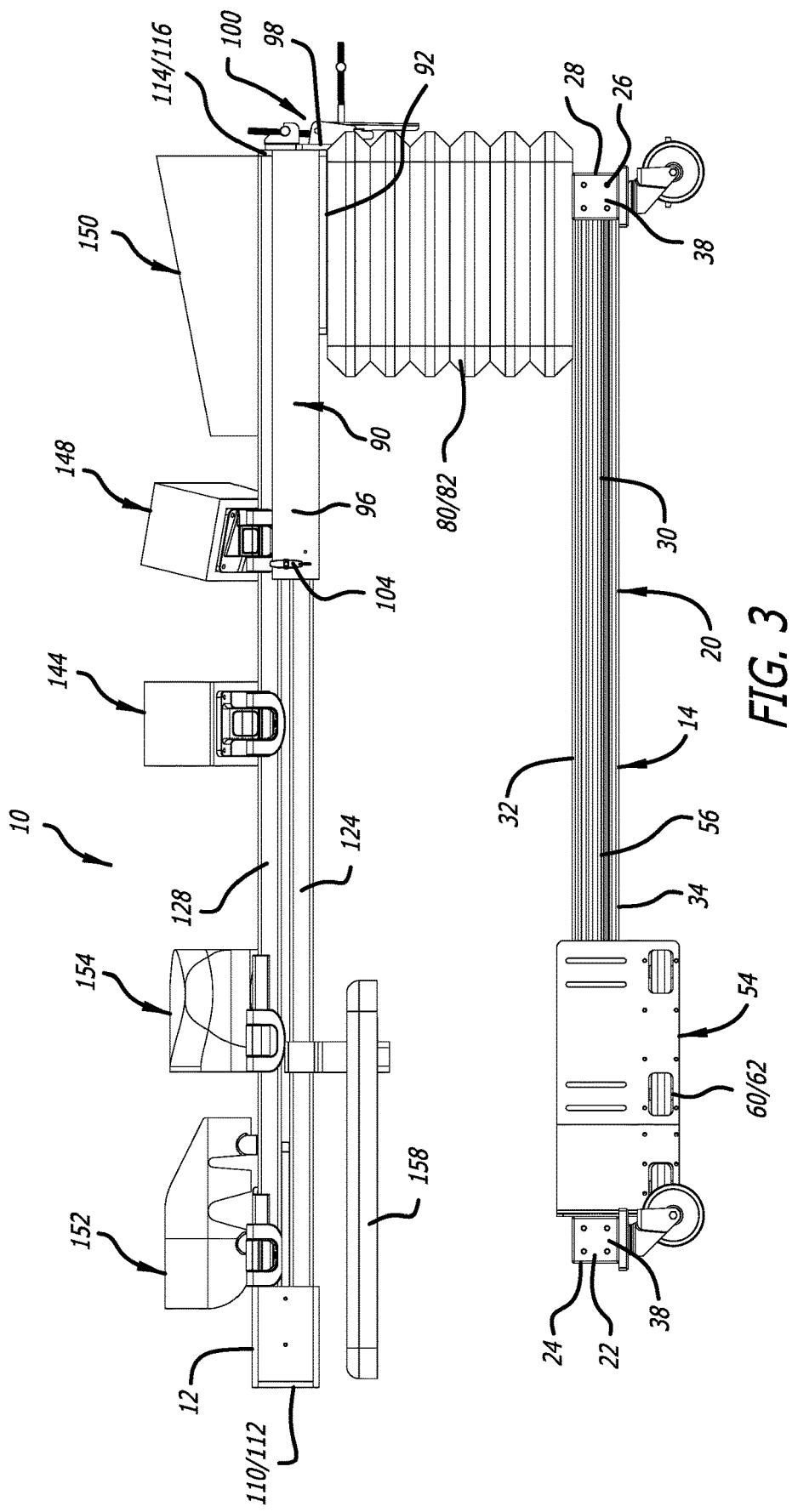
FIG. 3 is a second side, elevational view that illustrates the surgical platform and trolley assembly of FIG. 1.

As depicted in FIGS. 1-3, the trolley portion 14 includes a support structure 20 having a first end member 22 at a first end 24 thereof, a second end member 26 at a second end 28 thereof, and a cross member or cross members 30 extending between the first end member 22 and the second end member 26. The cross member(s) 30 can be aligned with a mid-longitudinal axis $L_2$ of the trolley portion 14, can be used to connect the first end member 22 and the second end member 26, and can be expandable and contractable to expand and contract a length of the trolley portion 14 along the mid-longitudinal axis $L_2$. Each of the first end member 22 and the second end member 26 includes an upper surface 32, a lower surface 34, a first lateral end 36, and a second lateral end 38. Furthermore, casters 40 can be attached relative to the lower surfaces 34 adjacent the first lateral ends 36 and the second lateral ends 38 of the of the first end member 22 and the second end member 26 to space the first end member 22 and the second end member 26 from the ground and to facilitate movement of the support structure 20.

Figure 5:
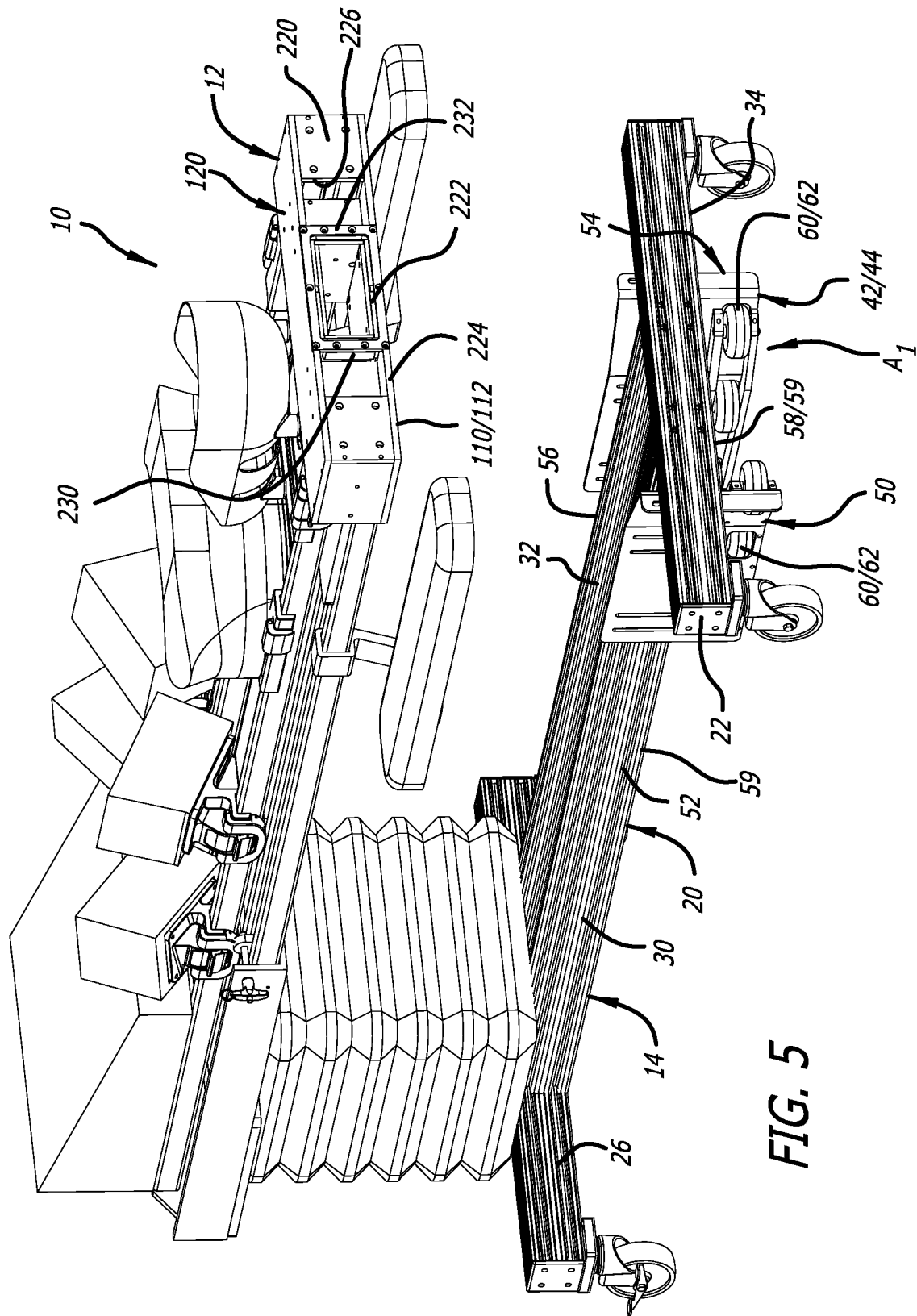
FIG. 5 is an end, side, perspective view that illustrates portions of a positioner included on the surgical platform and trolley assembly of FIG. 1 for facilitating positioning thereof relative to a surgical robotic system or robotic surgical guidance system.

The surgical platform and trolley assembly 10 initially can be positioned relative to the robotic system R using a positioner 42 having portions provided as part of the surgical platform and trolley assembly 10 and the robotic system R. To illustrate, the positioner 42 can include a receiver portion 44 that can be provided as part of the trolley portion 14, and a tongue portion 46 that can be attached to and/or provided as part of the robotic system R in FIGS. 6 and 11-15. The receiver portion 44 can be provided at and adjacent the first end 24, can be attached relative to and formed by portions of the first end member 22 and the cross member(s) 30. As depicted in FIG. 1, the receiver portion 44 includes a first plate portion 50 attached to a first lateral side surface 52 of the cross member(s) 30, a second plate portion 54 attached to a second lateral side surface 56 of the cross member(s) 30, and portions of a lower surface portion 58 of the first end member 22 and a lower surface portion 59 of the cross member(s) 30. Portions of the first plate portion 50 and the second plate portion 54 can extend below the lower surface portion 58 of the first end member 22 and the lower surface portion 59 of the cross member(s) 30, and, as depicted in FIGS. 1 and 5, the portions of the first plate portion 50 and the second plate portion 54 along with the lower surface portions 58 and 59 can define a receiving area or cavity $A_1$ for receiving the tongue portion 46. Each of the first plate portion 50 and the second plate portion 54 can include various apertures 60 adjacent the receiving area $A_1$ that are spaced therealong, and include various bumper wheels 62 rotatably mounted in the various apertures 60. Portions of the bumper wheels 62 can extend into the receiving area $A_1$. When the tongue portion 46 is received in the receiving area $A_1$, the bumper wheels 62 are used to both guide and position the tongue 46 relative the first plate portion 50 and the second plate portion 54 (and the remainder of the trolley assembly).

Figure 6:
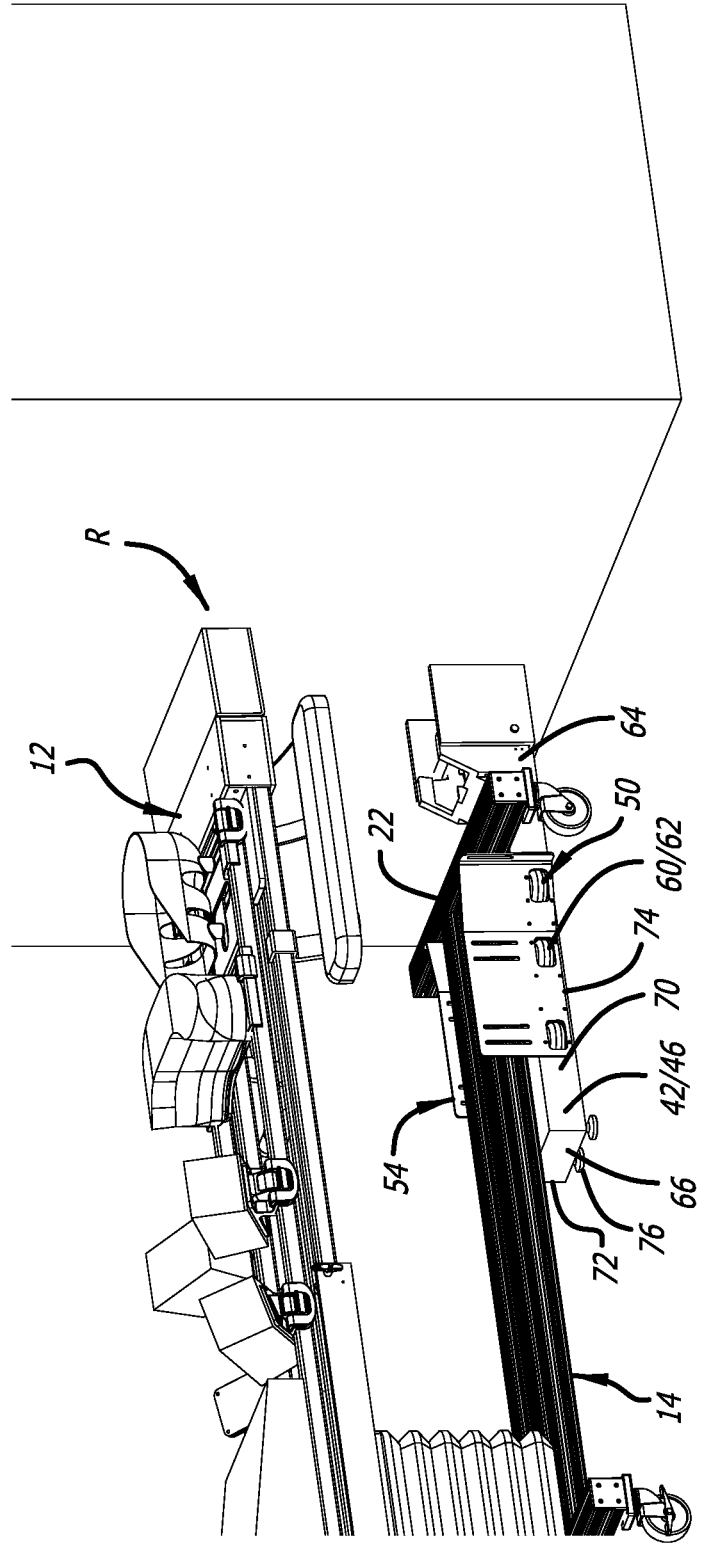
FIG. 6 is a side, perspective view that illustrates the portions of the positioner of the surgical platform and trolley assembly of FIG. 1 engaged to other portions of the positioner included on a representation of the surgical robotic system or robotic surgical guidance system.

The tongue portion 46, as depicted in FIGS. 6 and 11-15, is attached relative to the robotic system R, and includes a first end 64 and an opposite second end 66. As depicted in FIG. 6, the tongue portion 46 can include a first lateral side surface 70, a second lateral side surface 72, and a bottom surface 74 extending between the first end 64 and the second end 66. Adjustable feet 76 can be attached to the bottom surface 74 adjacent the second end 66 to facilitate leveling of at least portions of the tongue portion 46.

To initially position the trolley portion 14 (and the surgical platform portion 12 attached thereto) relative to the robotic system R, the trolley portion 14 can be positioned so that the tongue portion 46 is received in the receiver portion 44. In doing so, the tongue portion 46 is inserted between the first plate portion 50 and the second plate portion 54, under the first end member 22 and the cross member(s) 30, and into the receiving area $A_1$. As the tongue portion 46 is received in the receiving area $A_1$ (when the trolley portion 14 is properly positioned relative to the robotic system R), the first lateral side surface 70 contacts the bumper wheels 62 rotatably mounted to the first plate portion 50, and the second lateral side surface 72 contacts the bumper wheels 62 rotatably mounted to the second plate portion 54. Such contact affords relative movement of the tongue portion 46 to the receiver portion 44 that guides and positions the tongue portion 46 in the receiving area $A_1$ to initially position the surgical platform and trolley assembly 10 relative to the robotic system R. While the received portion 44 is attached relative to and formed by the trolley portion 14, and the tongue portion 46 is attached relative to the robotic system R, the positions of the receiver portion 44 and the trolley portion 46 can be reversed. And, while the manual insertion of the tongue portion 46 in the receiver portion 44 can serve to initially position the surgical platform and trolley assembly 10 relative to the robotic system R, an automatic interconnection mechanism (not shown) instead can be used for positioning the surgical platform and trolley assembly 10 and the robotic system R relative to one another.

As depicted in FIGS. 1-3, the trolley portion 14 includes a lifting/adjustment portion 80 for orienting and reorienting the surgical platform portion 12 relative to the trolley portion 14. A lower portion of the lifting/adjustment portion 80 is supported by the second end member 26 and the cross member(s) 30. To orient and reorient the surgical platform portion 12, the lifting/adjustment portion 80 can be expanded and contracted in height between a fully-expanded position and a fully-contracted position, respectively, to correspondingly raise and lower the surgical platform portion 12 relative to the first end member 22, the second end member 24, and the cross member(s) 30; the lifting/adjustment portion 80 can be tilted backward and forward relative to the first end 22 to tip the surgical platform portion 12 upwardly and downwardly relative to the cross member(s) 30 to change the angle of the surgical platform portion 12 in a vertical plane aligned with the mid-longitudinal axes $L_1$ and $L_2$; and the lifting/adjustment portion 80 can be tilted side-to-side relative to the cross-members 30 in a vertical plane perpendicular to the vertical plane aligned with the mid-longitudinal axes $L_1$ and $L_2$.

The mechanical portions (not shown) of the lifting/adjustment portion 80 affording such movement can be contained with an accordion shroud 82, and such mechanical portions can be includes various linkages, lifters, rotators, and pivoters, along with one or more actuators (not shown) that drive such movement using such mechanical componentry. The actuator(s) can be controlled by the controller(s) of the surgical platform and trolley assembly 10 and/or the robotic system R. The operation of the lifting/adjustment portion 80 can be used to position the surgical platform portion 12 in the proper orientation to facilitate surgery on the patient P positioned thereon, and/or in the proper orientation to facilitate interconnection of the surgical platform portion 12 with the robotic system R. For example, after the tongue portion 46 is received in the receiver portion 44, the controller(s) of the surgical platform and trolley assembly 10 and/or the robotic system R can control operation of the lifting/adjustment portion 80 to position the surgical platform portion 12 for engagement relative to the robotic system R.

As depicted in FIGS. 1-4, 9, and 10, the trolley portion 14 also includes a cradle portion 90 supported by an upper portion of the lifting/adjustment portion 80 for connecting the surgical platform portion 12 to the trolley portion 14. As discussed below, the cradle portion 90 can be connected with and disconnected from the surgical platform portion 12 to facilitate attachment and detachment thereof relative to the trolley portion 14. The cradle portion 90 can include a base portion 92, a first side portion 94, a second side portion 96, and an end portion 98. The base portion 92, the first side portion 94, the second side portion 96, and/or the end portion 98 can be attached to one another, and/or attached directly to the upper portion of the lifting/adjustment portion 80. In some embodiments, for example, some of the base portion 92, the first side portion 94, the second side portion 96, and/or the end portion 98 can be attached to the mechanical portions of the lifting/adjustment portion 80.

Various latches and/or pins can be used to maintain the attachment between the surgical platform portion 12 and the cradle portion 90 (and the trolley portion 14) to facilitate attachment of the surgical platform portion 12 relative to the trolley portion 14. For example, as depicted in FIGS. 2-4, 9, and 10, a latch mechanism 100 can be attached to portions of the end portion 98 and portions of the surgical platform portion 12, a first pin 102 can be inserted through the first side portion 94 and portions of the surgical platform portion 12, and a second pin 104 can be inserted through the second side portion 96 and portions of the surgical platform portion 12. Engagement of the latch mechanism 100, the first pin 102, and the second pin 104 serves in connecting the surgical platform portion 12 to the cradle portion 90. With the surgical platform portion 12 attached relative to the trolley portion 14, the surgical platform portion 12 can be moved using the casters 40 and the lifting/adjustment portion 80.

As depicted in FIGS. 1-4, the surgical platform portion 12 includes a first end portion 110 at and adjacent a first end 112 thereof, a second end portion 114 at and adjacent a second end 116 thereof, and various rails positioned therebetween that connect the first end portion 110 and the second end portion 114 to one another. As discussed below, the first end portion 110 includes an engagement portion 120 for interfacing with portions of the robotic system R to facilitate interconnection of the surgical platform portion 12 with the robotic system R, and the second end portion 114 and some of the various rails are interconnectable with the cradle portion 90.

The various rails, as depicted in FIGS. 1-4, can include a first outer rail 122, a second outer rail 124, a first inner rail 126, and/or a second inner rail 128 that extend between the first end portion 110 and the second end portion 114. First end portions of the first outer rail 122, the second outer rail 124, the first inner rail 126, and/or the second inner rail 128 can be attached relative to the first end portion 110, opposite second end portions of the first outer rail 122, the second outer rail 124, the first inner rail 126, and/or the second inner rail 128 can be attached relative to the second end portion 114, and/or the first and second end portions can be attached to intermediate portions (not shown) positioned between the various rails and the first end portion 110 and/or the second end portion 114. Furthermore, the first outer rail 122, the second outer rail 124, the first inner rail 126, and the second inner rail 128 can be aligned with a mid-longitudinal axis L3 of the surgical platform portion 12 with the first outer rail 122 and the first inner rail 126 being positioned on one side of the mid-longitudinal axis L3, and the second outer rail 124 and the second inner rail 128 being positioned on the other side of the mid-longitudinal axis L3.

The second end portion 114 can include a portion of the latch mechanism 100, the first outer rail 122 can include a first hole 130 for receiving the first pin 102, and the second outer rail 124 can include a second hole 132 for receiving the second pin 104. Engagement between portions of the latch mechanism 100, receipt of the first pin 102 in the first hole 130, and receipt of the second pin 104 in the second hole 132 maintains attachment between the surgical platform portion 12 to the cradle portion 90. As depicted in FIGS. 1-3, such engagement allows portions of the surgical platform portion 12 to be cantilevered over the trolley portion 14. The first outer rail 122, the second outer rail 124, the first inner rail 126, and/or the second inner rail 128 can provide structural rigidity to the surgical platform portion 12, and permit the surgical platform portion 12 to extend outwardly from the cradle portion 90 over portions of the support structure 20 of the trolley portion 14. As such, the cantilevering of portions of the surgical platform portion 12 provides space under portions of the surgical platform portion 12 and between the portions of the surgical platform portion 12 and the portions of the support structure 20 of the trolley portion 14, and such space, for example, can be used to facilitate use of an O-arm, a C-arm, and/or other electromagnetic imaging device for electromagnetic imaging of the patient P. That is, given the arrangement of the surgical platform portion 12 and the support structure 20 of the trolley portion 14 relative to one another, portions the O-arm, the C-arm, and/or the other electromagnetic imaging device can be received both over and under the patient P supported by the surgical platform portion 12. Furthermore, all or portions (especially, portions thereof adjacent the spine of the patient P) of the first outer rail 122, the second outer rail 124, the first inner rail 126, and/or the second inner rail 128, and/or other portions of the surgical support platform 12 can be made of a radiographically transparent material to enhance use of the electromagnetic imaging of the patient P.

In addition to providing structural rigidity to the surgical platform portion 12, the first outer rail 122, the second outer rail 124, the first inner rail 126, and/or the second inner rail 128 also can be used to support various patient support portions of the surgical platform portion 12. Some or all of the various patient support portions can be moveably adjusted or fixed in position along portions of the first outer rail 122, the second outer rail 124, the first inner rail 126, and/or the second inner rail 128 to accommodate differently-sized patients. Furthermore, straps (not shown) could also be used to secure the portions of the patient P to these portions of the surgical platform portion 12.

As depicted in FIGS. 9-15, the patient P can be supported in a prone position by the various patient support portions, and, as depicted in FIGS. 1-4, the various patient support portions can include a head and chest support portion 140, a first upper thigh support 142, a second upper thigh support 144, a first lower thigh support 146, a second lower thigh support 148, a lower leg support 150, a first arm support 156, and a second arm support 158 that are supported by portions of the first inner rail 126 and/or the second inner rail 128. The head and chest support portion 140, the first upper thigh support 142, the second upper thigh support 144, the first lower thigh support 146, the second lower thigh support 148, and/or the lower leg support 150 can be moveably adjusted or fixed in position along the first inner rail 126 and/or the second inner rail 128. The head and chest support portion 140, the first upper thigh support 142, the second upper thigh support 144, the first lower thigh support 146, the second lower thigh support 148, and/or the lower leg support 150 could also or alternatively be supported (moveably adjusted or in a fixed position therealong) by the first outer rail 122 and/or the second outer rail 124.

Figure 4:
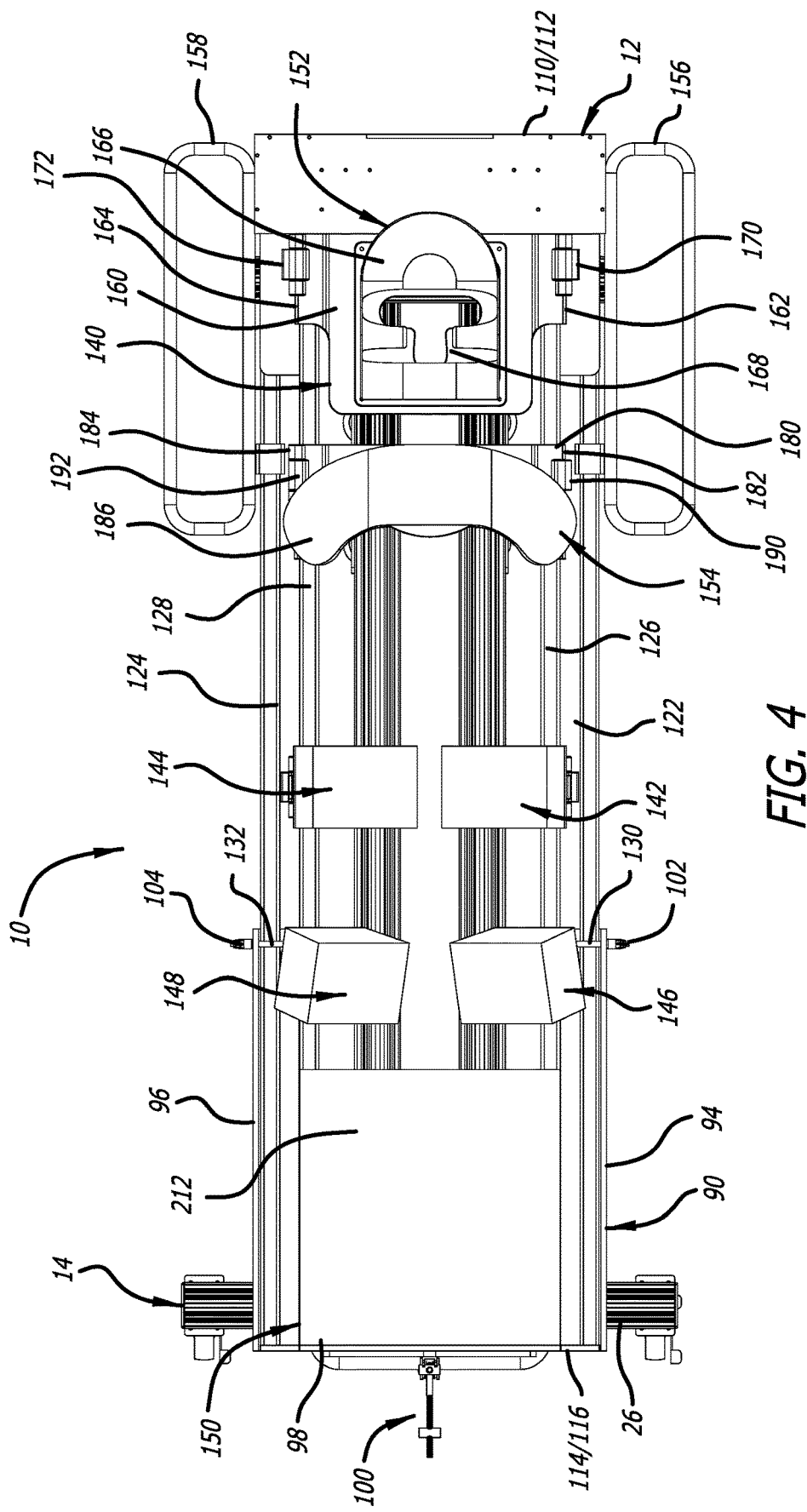
FIG. 4 is a top, plan view that illustrates the surgical platform and trolley assembly of FIG. 1.

As depicted in FIG. 4, portions of the head and chest support portion 140 are moveably supported by the first inner rail 126 and the second inner rail 128, the first upper thigh support 142 is moveably supported by the first inner rail 126, the second upper thigh support 144 is moveably supported by the second inner rail 128, the first lower thigh support 146 is moveably supported by the first inner rail 126, the second lower thigh support 148 is moveably supported by the second inner rail 128, and the lower leg support 150 is fixed in position relative to the first inner rail 126 and the second inner rail 128. As such, the first inner rail 126 and the second inner rail 128 serve as tracks affording adjustment therealong of the head and chest support 140, the first upper thigh support 142, the second upper thigh support 144, the first lower thigh support 146, and the second lower thigh support 148 therealong.

The head and chest support portion 140 can include a head support and a chest support that are integrated with one another, or the head and chest support portion 140, as depicted in FIGS. 1-4, can include a head support 152 and a chest support 154 that are separate from one another. The head support 152, as depicted in FIG. 4, includes a first platen portion 160, a first lateral side portion 162 attached relative to a first lateral side of the first platen portion 160, and a second lateral side portion 164 attached relative to a second lateral side of the first platen portion 160. The first platen portion 160 can extend between the first lateral side portion 162 and the second lateral side portion 164, and, using the first lateral side portion 162 and the second lateral side portion 164, the first platen portion 160 can be supported between the first inner rail 126 and the second inner rail 128. As depicted in FIG. 4, the first platen portion 160 can be used to support head support structure 166 thereon, and can include an aperture or apertures 168 formed therein (and through the head support structure 166) that can provide access to the airways of the patient P. Furthermore, the first lateral side portion 162 can contact and be moveably supported by the first inner rail 126, and the second lateral side portion 164 can contact and be moveably supported by the second inner rail 128. Additionally, the first lateral side portion 162 can include a first clamping portion 170 attached thereto, and the second lateral side portion 164 can include a second clamping portion 172 attached thereto that can, respectively, be engaged and disengaged relative to the first inner rail 126 and the second inner rail 128.

Engagement of the first clamping portion 170 and the second clamping portion 172 maintains the first lateral side portion 162 and the second lateral side portion 164 (and the first platen portion 160) in position relative to the first inner rail 126 and the second inner rail 128, respectively, and disengagement of the first clamping portion 170 and the second clamping portion 172 allows movement of the first lateral side portion 162 and the second lateral side portion 164 (and the first platen portion 160) along the first inner rail 126 and the second inner rail 128, respectively. As such, the head support structure 166 can be positioned and repositioned to accommodate patients of different sizes to find an acceptable position to support the patient's head, and then the head support structure 166 can be maintained in position using the first clamping portion 170 and the second clamping portion 172.

In similar fashion to the head support 152, the chest support 154 can include a second platen portion 180, a first lateral side portion 182 attached relative to a first lateral side of the second platen portion 180, and a second lateral side portion 184 attached relative to a second lateral side of the second platen portion 180. The second platen portion 180 can extend between the first lateral side portion 182 and the second lateral side portion 184, and, using the first lateral side portion 182 and the second lateral side portion 184, the second platen portion 180 can be supported between the first inner rail 126 and the second inner rail 128. As depicted in FIG. 4, the second platen portion 180 can be used to support and attach chest support padding 186. Furthermore, the first lateral side portion 182 can contact and be moveably supported by the first inner rail 126, and the second lateral side portion 184 can contact and be moveably supported by the second inner rail 128. Additionally, the first lateral side portion 182 can include a first clamping portion 190 attached thereto, and the second lateral side portion 184 can include a second clamping portion 192 attached thereto that can, respectively, be engaged and disengaged relative to the first inner rail 126 and the second inner rail 126.

Engagement of the first clamping portion 190 and the second clamping portion 192 maintains the first lateral side portion 182 and the second lateral side portion 184 (and the second platen portion 180) in position relative to the first inner rail 126 and the second inner rail 128, respectively, and disengagement of the first clamping portion 190 and the second clamping portion 192 allows movement of the first lateral side portion 182 and the second lateral side portion 184 (and the second platen portion 180) along the first inner rail 126 and the second inner rail 128, respectively. As such, the chest support padding 186 can be positioned and repositioned to accommodate patients of different sizes to find an acceptable position to support the patient's chest, and then the chest support padding 186 can be maintained in position using the first clamping portion 190 and the second clamping portion 192.

If the head support and the chest support are integrated with one another, portions of the head support and the chest support can be included on a single platen (not shown) that can be moveably supported by the first inner rail 126 and the second inner rail 128, and these portions of the head support and the chest support also can be moveably supported relative to the single platen. The single platen, as well as the head support and the chest support when moveably supported by the single platen, can include one or more clamping portions attached thereto for maintaining the single platen, the head support, and/or the chest support in position.

The first upper thigh support 142, the second upper thigh support 144, the first lower thigh support 146, and the second lower thigh support 148 can each include bracket portions 200, support padding 202, and clamping portions 204. The bracket portions 200 of the first upper thigh support 142, the second upper thigh support 144, the first lower thigh support 146, and the second lower thigh support 148 can be moveably supported relative to at least one of the first outer rail 122, the second outer rail 124, the first inner rail 126, and/or the second inner rail 128. As depicted in FIGS. 1-4, the bracket portions 200 of the first upper thigh support 142 and the first lower thigh support 146 are moveably supported by the first inner rail 126, and the bracket portions 200 of the second upper thigh support 144 and the second lower thigh support 148 are moveably supported by the second inner rail 128.

The bracket portions 200 can each include plate portions 206 for supporting and attaching the support padding 202, and the plate portions 206 of the first upper thigh support 142, the second upper thigh support 144, the first lower thigh support 146, and the second lower thigh support 148 can have different angles with respect to the remainders of the bracket portions 200 to orient the support padding 202 differently. The clamping portions 204, like the clamping portions discussed above, can be engaged and disengaged to the first inner rail 126 and/or the second inner rail 128 to maintain the positions thereof or allow the positioning and repositioning therealong. As such, the first upper thigh support 142, the second upper thigh support 144, the first lower thigh support 146, and the second lower thigh support 148 can be adjusted into position to accommodate patients of different sizes, and then the first upper thigh support 142, the second upper thigh support 144, the first lower thigh support 146, and the second lower thigh support 148 can be maintained in position using the clamping portions 204.

The lower leg support 150 includes a plate portion 210 and support padding 212. The plate portion 210 is positioned between and supported by the first inner rail 126 and the second inner rail 128, and the support padding 212 is supported by and attached to the plate portion 210. The plate portion 210, as depicted in FIG. 1, is fixed in position relative to the first inner rail 126 and the second inner rail 128. However, like the other various patient support portions, the plate portion 210 can be moveably supported relative to the remainder of the surgical platform portion 12 to afford positioning and repositioning thereof, and can include one or more clamping portions that can be engaged and disengaged. As such, when adjustably attached between the first inner rail 126 and the second inner rail 124, the lower leg support 150 can be adjusted into position to accommodate patients of different sizes, and then the lower leg support 150 can be maintained in position using the one or more clamping portions.

With the head and chest support portion 140, the first upper thigh support 142, the second upper thigh support 144, the first lower thigh support 146, the second lower thigh support 148, and/or the lower leg support 150 positioned to accommodate the size of the patient P, the patient P can be received on and supported by the surgical platform portion 12 Furthermore, the operation of the lifting/adjustment portion 80 can be used to position the surgical platform portion 12 in the proper orientation to facilitate surgery on the patient P positioned thereon, and/or in the proper orientation to facilitate interconnection of the surgical platform portion 12 to the robotic system R. As depicted in FIGS. 9-15, the patient P can be positioned head-first relative to the robotic system R. With surgical platform portion 12 properly oriented and positioned relative to the robotic system R using the trolley portion 14, the surgical platform portion 12 then can be interconnected relative to the robotic system R. The engagement portion 120 of the first end portion 110 of the surgical platform portion 12, as depicted in FIGS. 7A, 7B, 9, and 10, can be used in facilitating the interconnection with the robotic system R.

The first end portion 110 includes an end surface 220 at the first end 112 of the surgical platform portion 12. The engagement portion 120 can include one or more openings for receiving complimentary structures included with the robotic system R or a sub-system (not shown) positioned relative to the robotic system R. The one or more openings of the engagement portion 120 can include one or more primary openings and one or more secondary openings. As depicted in FIGS. 1, 7A, 7B, 8A, and 8B, the engagement portion 120 includes a single primary opening 222 formed through the end surface 220 and into the first end portion 110, a first secondary opening 224 on a side of the primary opening 222 formed through the end surface 220 and into the first end portion 110, and a second secondary opening 226 on another side of the primary opening 222 formed through the end surface 220 and into the first end portion 110. The engagement portion 120 also can include one or more lip portions for engaging complimentary structures included with the robotic system R.

Figure 7A:
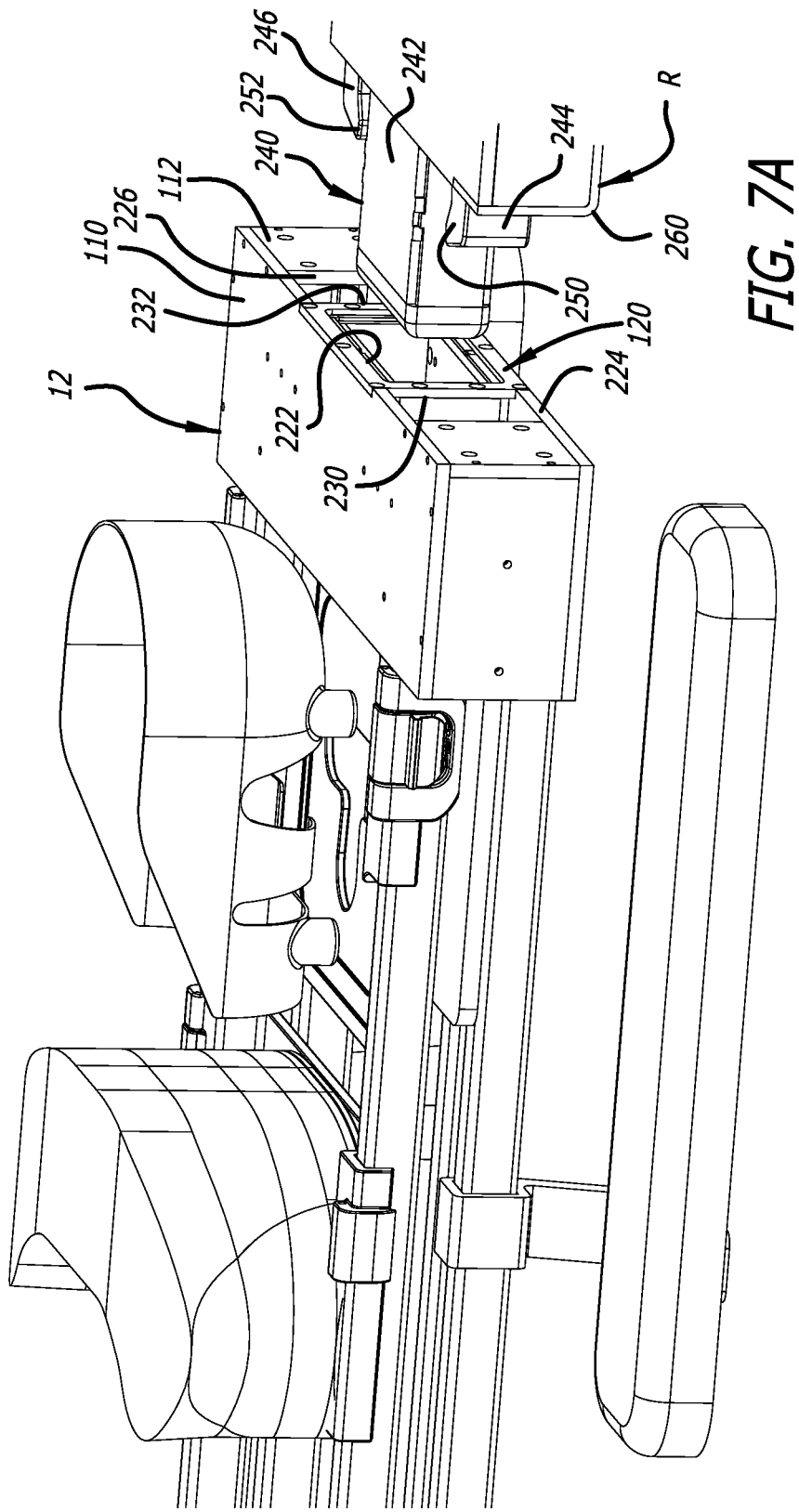
FIG. 7A is a side, perspective view that illustrates complimentary portions of the platform portion of the surgical platform and trolley assembly of FIG. 1 positioned adjacent corresponding complimentary portions incorporated in the representation of the surgical robotic system or robotic surgical guidance system.
Figure 8A:
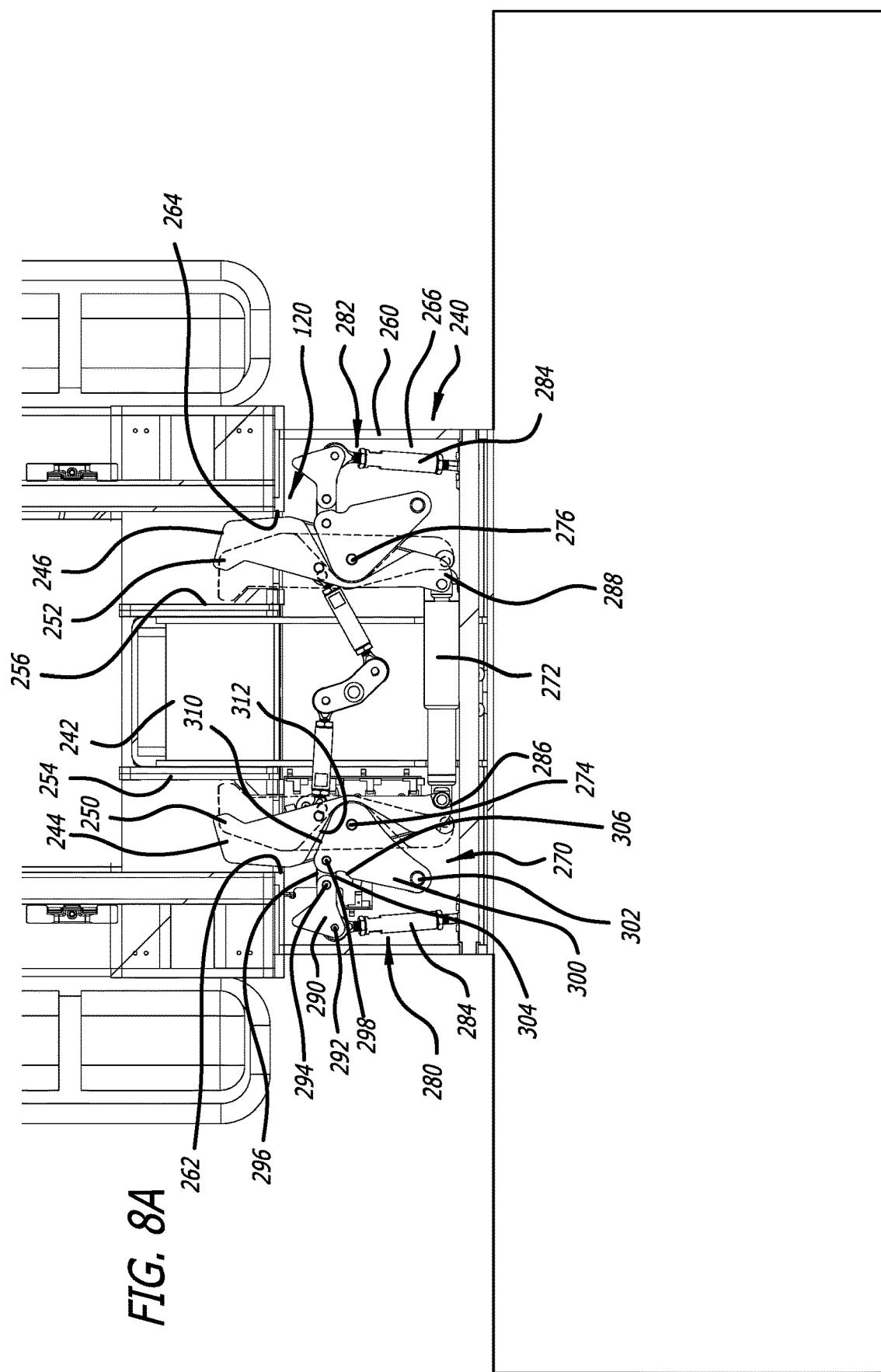
FIG. 8A is a top, plan, fragmentary view that illustrates the attachment of the complimentary portions of FIGS. 7A and 7B.
Figure 8B:
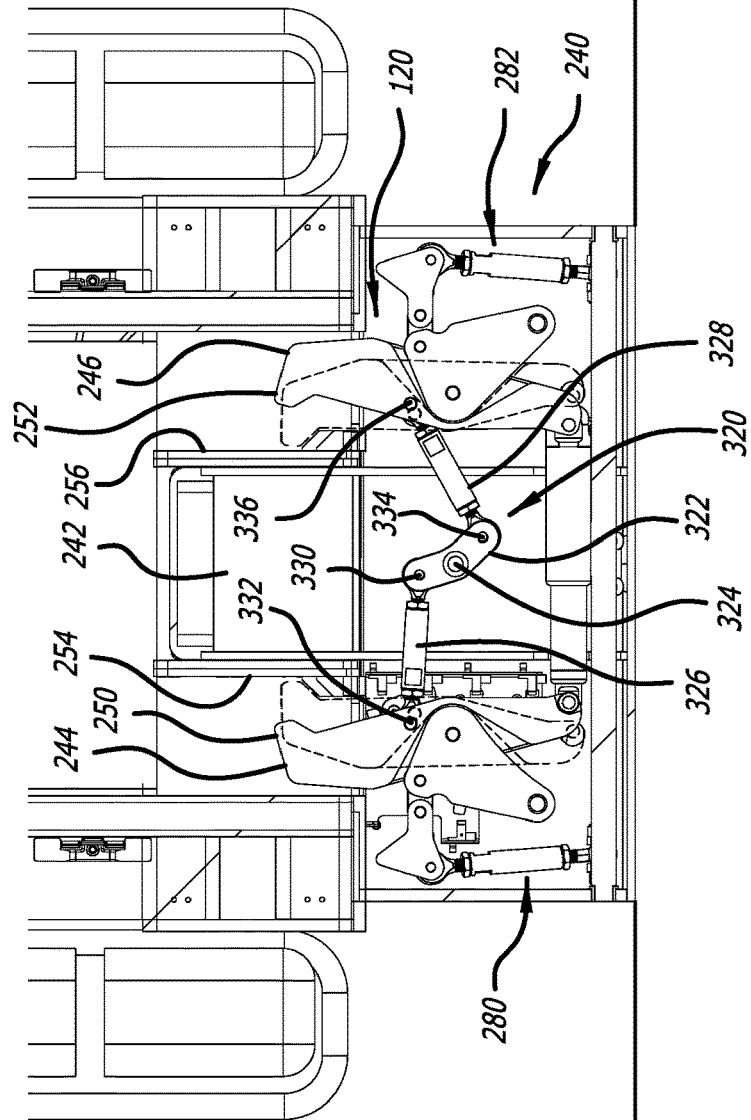
FIG. 8B is a top, plan, fragmentary view that also illustrates the attachment of the complimentary portions of FIGS. 7A and 7B.
Figure 9:
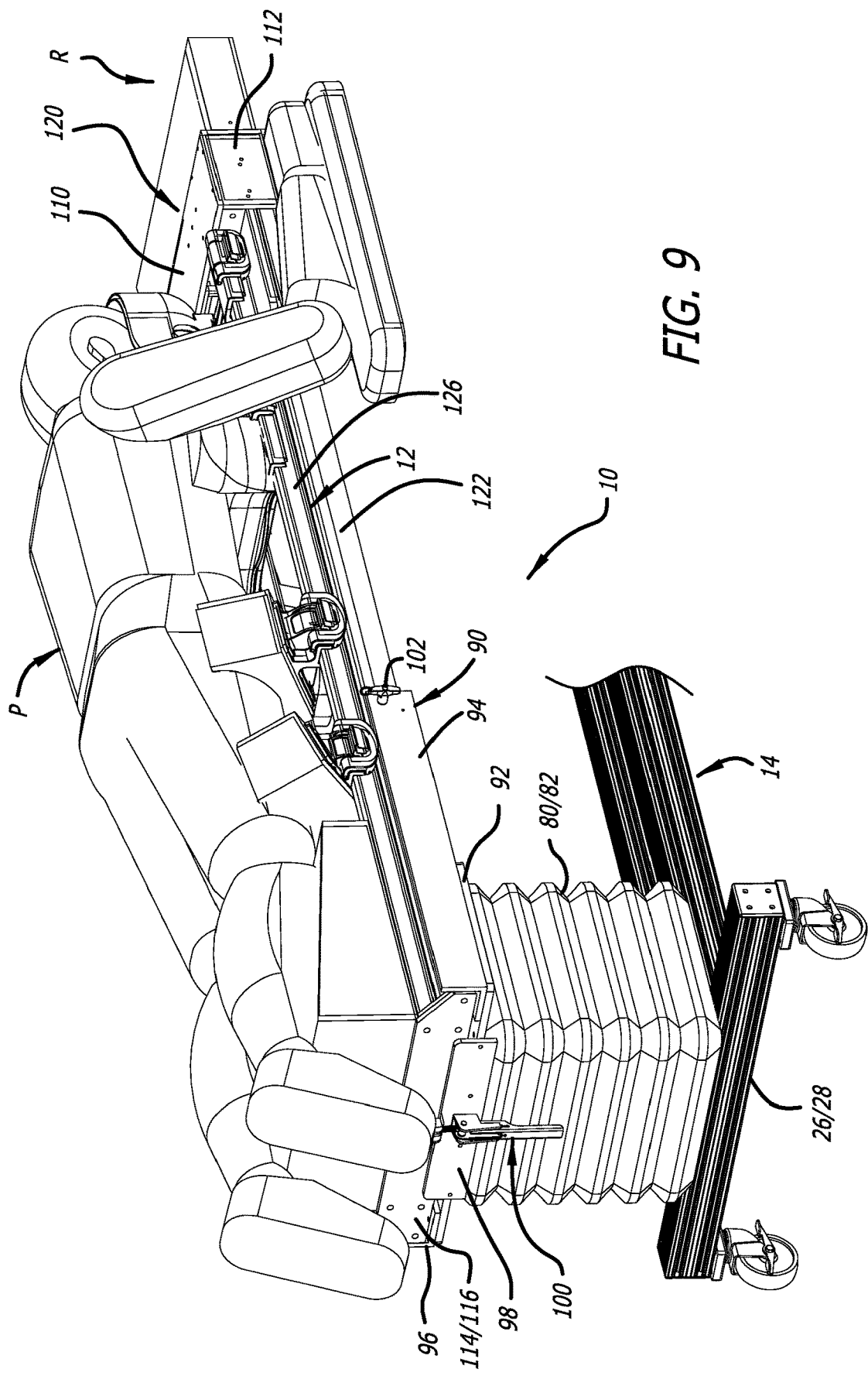
FIG. 9 is an end, side, perspective view of the platform portion of the surgical platform and trolley assembly of FIG. 1 and a patient positioned thereon attached relative to the representation of the surgical robotic system or robotic surgical guidance system with the platform portion connected to the trolley portion.
Figure 10:
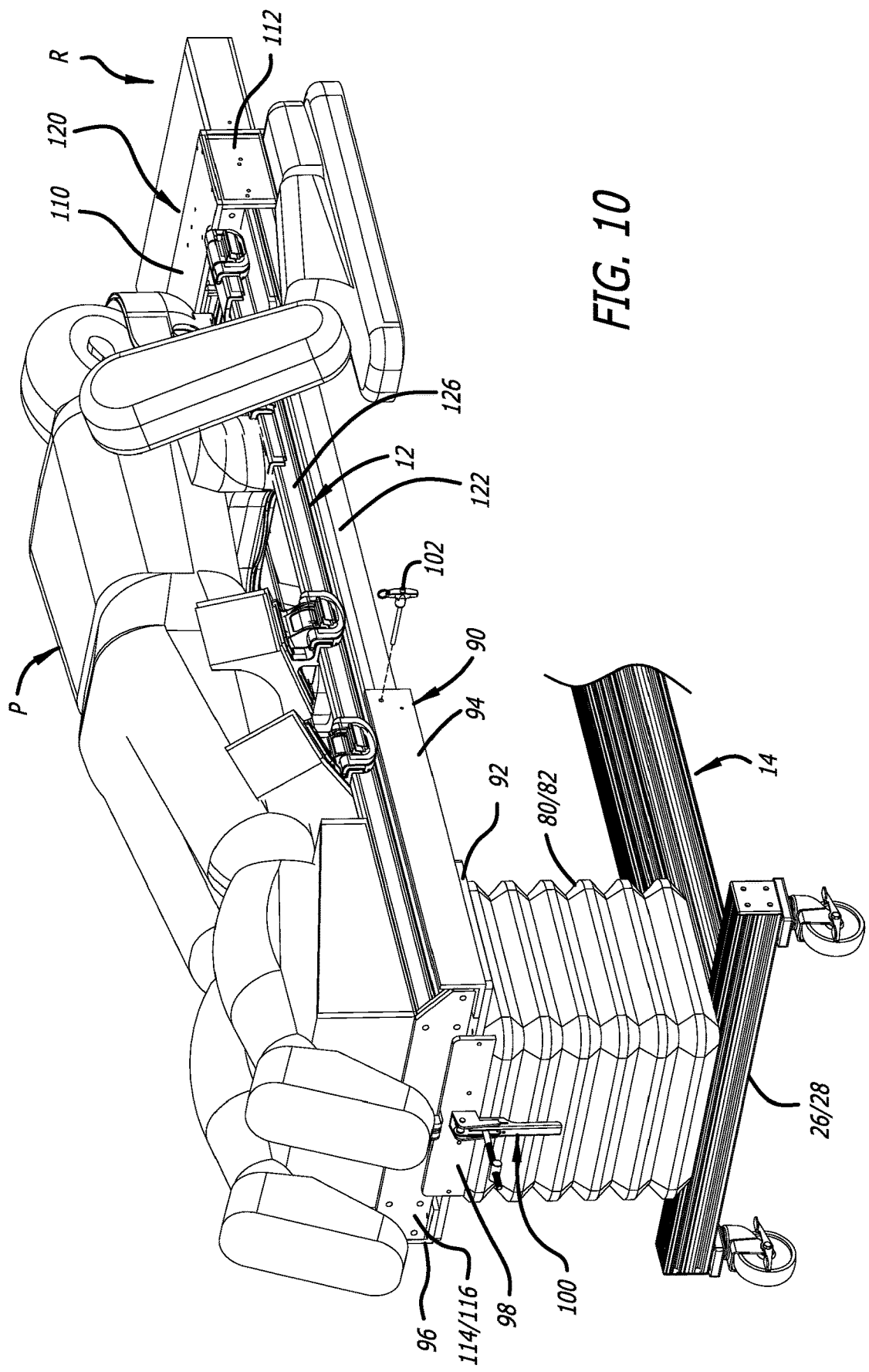
FIG. 10 is an end, side, perspective view of the platform portion of the surgical platform and trolley assembly of FIG. 1 and the patient positioned thereon attached relative to the representation of the surgical robotic system or robotic surgical guidance system with the platform portion disconnected from the trolley portion.

As depicted in FIGS. 7A, 8A, and 8B, the engagement portion 120 includes a first lip portion 230 formed by a portion of the first end portion 110 inside the first secondary opening 224 adjacent the primary opening 222, and a second lip portion 232 formed by a portion of the first end portion 110 inside the second secondary opening 226 adjacent the primary opening 222. While the primary opening 222 is centrally located with respect to the first end portion 110 and the first and second secondary openings 224 and 226, the engagement portion 120 is not limited thereto. The primary opening or openings, as well as the secondary opening or openings, can be located in different locations in the first end portion 110. And the lip portion or lip portions also can be located in different locations on the first end portion 110.

The robotic system R or the sub-system positioned relative to the robotic system R includes the complimentary structures that interface with the engagement portion 120 to interconnect the surgical platform portion 12 with the robotic system R. The complimentary structures are formed by a complimentary engagement portion 240, and the complimentary engagement portion 240 can include one or more tongue portions and one or more catch portions positioned relative to the tongue portions. The complimentary engagement portion 240, as depicted in FIGS. 7A, 8A, and 8B, includes a single tongue portion 242 for receipt within the primary opening 222, a first catch portion 244 for receipt in the first secondary opening 224, and a second catch portion 246 for receipt in the second secondary opening 226. As depicted in FIGS. 7A, 8A, and 8B, the tongue portion 242 is fixed in position, and the first and second catch portions 244 and 246 are moveable relative to the tongue portion 242. While the first end portion 110 of the surgical platform portion 12 includes the engagement portion 120, and the robotic system R or the sub-system positioned relative to the robotic system R includes the complimentary engagement portion 240, the positions of the engagement portion 120 and the complimentary engagement portion 240 can be reversed.

Depending on the number and locations of the primary openings and secondary openings formed in the first end portion 110, the number and locations of the tongue portions and the catch portion can be accordingly adjusted. Furthermore, the sizes of the tongue portion or portions can correspond to the size of the primary opening or openings, and the sizes of the catch portion or portion can correspond to the size of the secondary opening or openings. As depicted in FIG. 7A, the tongue portion 242 is sized in height and width (perpendicular to the mid-longitudinal axis L3 of the surgical platform portion 12) to fit within the primary opening 224 such that there is limited play therebetween. That is, the differences between the height and width of the tongue portion 242 and the height and width of the primary opening 222 (also perpendicular to the mid-longitudinal axis L3 of the surgical platform portion 12) are small enough (provided the tongue portion 242 is inserted an adequate depth into the primary opening 222) to limit downward and side-to-side movement of the surgical platform portion 12 relative to the robotic system R or the sub-system. The first and second catch portions 244 and 246 can likewise have heights for which the differences between the heights of the catch portions and the heights of the first and second secondary openings 224 and 226 are small enough (provided the first and second catch portions 244 and 246 are inserted an adequate depth in the first and second secondary openings 224 and 226, respectively) to limit downward movement of the surgical platform portion 12 relative to the robotic system R or the sub-system.

The first and second catch portions 244 and 246 can include a first hook portion 250 and a second hook portion 252 at distal ends of thereof, respectively, for engaging portions of the first end portion 110. For example, the first secondary opening 224 can include the first lip portion 230 and a first sidewall portion 254 with which the first hook portion 250 is engageable, and the second secondary opening 226 can include the second lip portion 232 and a second sidewall portion 256 with which the second hook portion 252 is engageable after receipt of the first catch portion 244 and the second catch portion 246, respectively, into the first and second openings 244 and 246. And, as depicted in FIGS. 8A and 8B, the first and second catch portions 244 and 246 are moveable between a disengaged first position and an engaged second position (shown in broken lines) to facilitate such engagement. In the disengaged first positions, the first and second catch portions 244 and 246 are insertable into the first and second secondary apertures 224 and 226, respectively, and in the engaged second positions, the first and second catch portions 244 and 246 are engageable with the first and second lip portions 230 and 232 and/or the first and second sidewall portions 254 and 256, respectively, to afford positive engagement of the complimentary engagement portion 240 to the engagement portion 120 (and the surgical platform portion 12). The interconnection of the surgical platform portion 12 to the robotic system R or the subsystem formed via receipt of the tongue portion 242 in the primary opening 222, receipt and engagement of the first catch portion 244 in the first secondary opening 224, receipt and engagement of the second catch portion 246 in the second secondary opening 226, and the respective engagement of the first hook portion 250 and the second hook portion 252 with the first and second lip portions 230 and 232 and/or the first and second sidewall portions 254 and 256 serves to interconnect and hold the surgical platform portion 12 in position relative to the robotic system R.

As depicted in FIGS. 7A, 7B, 8A, and 8B, the complimentary engagement portion 240 of the robotic system R includes a housing portion 260 that contains portions of the first and second catch portions 244 and 246. The tongue portion 242, as depicted in FIGS. 8A and 8B, extends outwardly from the housing portion 260, and a first opening 262 is provided on a side of the tongue portion 242, and a second opening 264 is provided on another side of the tongue portion 242. Portions of the first and second catch portions 244 and 246 are provided in an interior 266 of the housing portion 260, other potions of the first catch portion 244 (including the first hook portion 250) can extend through the first opening 262, and other portions of the second catch portion 246 (and the second hook portion 252) can extend through the second opening 264. As discussed below, the complimentary engagement portion includes an actuator mechanism 270 provided in the interior 266 for facilitating movement of the first and second catch portions 244 and 246 between the disengaged first positions and the engaged second positions thereof. The actuator mechanism 270 can be controlled by the one or controllers of the surgical platform and trolley assembly 10 and/or the robotic system R.

As depicted in FIG. 8A, the actuator mechanism 270 includes an actuator 272 connecting the first and second catch portions 244 and 246 to one another. The first catch portion 244 includes an end portion 286 (opposite from the first hook portion 250) that is pinned to one end of the actuator 272, and the second catch portion 246 includes an end portion 288 (opposite from the second hook portion 252) that is pinned to the other end of the actuator 272. The first catch portion 244 is pivotable about a pin 274, the second catch portion 246 is pivotable about a pin 276, and expansion of the actuator 272 pivots the first catch portion 244 about the pin 274 and pivots the second catch portion 246 about the pin 276 to move the first and second catch portions 244 and 246 from the disengaged first positions to the engaged second positions. As such, expansion of the actuator 272 presses the first and second catch portions 244 and 246 against the first and second lip portions 230 and 232 and/or the first and second sidewall portions 254 and 256, respectively, to secure attachment of the complimentary engagement portion 240 to first end portion 110. And contraction of the actuator 272 moves the first and second catch portions 244 and 246 from the engaged second positions to the disengaged first positions.

The actuator mechanism 270 also includes two first locking mechanisms 280 and 282 that are used for maintaining the first and second catch portions 244 and 246, respectively, in the engaged second position. Each of the first locking mechanisms 280 and 282 can includes an actuator 284 attached at one end to the housing 260 that can drive movement of the first locking mechanisms 280 and 282. Each of the first locking mechanisms 280 and 282 also can include a first cam 290 having a pinned connection 292 to the actuator 284 and a pinned connection 294 to a linkage 296, the linkage 296 having a pinned connection 298 to a second cam 300, and the second cam 300 having a pinned connection 302 to the housing 260, and being connected to one of the first and second catch portions 244 and 246 via the corresponding pins 274 and 276.

As depicted in FIG. 8A, with the first and second catch portions 244 and 246 in the engaged second position, the first locking mechanisms 280 and 282 can be actuated to maintain the position of the first and second catch portions 244 and 246. In doing so, the actuator 284 of each of the first locking mechanisms 280 and 282 can be actuated (via expansion thereof) to move the first cam 290 about the pinned connections 292 and 294. Correspondingly, the linkage 296 also moves (via actuation of the actuator 284) about the pinned connection 294 and the pinned connection 298, and in doing so, an end portion 304 of the first cam 290 is forced into an indentation 306 formed in the second cam 300. The interaction of the end portion 304 in the indentation 306 (via actuation of the actuator 284) pushes the second cam 300 to move about the pinned connection 302, and forces a contact surface 310 of the second cam 300 against a contact surface 312 of the of the one of the first and second catch portions 244 and 246. The force of the contact surface 310 against the contact surface 312 at the very least prevents the first and second catch portion 244 and 246 from moving away from the engaged second position, and can serve to increase pressure of the first and second catch portions 244 and 246 on the first and second lip portions 230 and 232 and/or the first and second sidewall portions 254 and 256, respectively, to further secure attachment of the complimentary engagement portion 240 to first end portion 110. As such, the actuation of the first locking mechanisms 280 and 282 can serve maintaining the interconnection of the surgical platform portion 12 to the robotic system R or the sub-system.

To allow the first and second catch portions 244 and 246 to move from the engaged second position to the disengaged first position after use of the first locking mechanisms 280 and 282, the first locking mechanisms 280 and 282 can be actuated to release the first and second catch portions 244 and 246, respectively. In doing so, the actuators 284 of each of the first locking mechanisms 280 and 282 can be actuated (via contraction thereof) to move the first cam 290, the linkage 296, and the second cam 300 in order to move the contact surface 310 away from the contact surface 312. Given the arrangement of the first cam 290, the linkage 296, and the second cam 300, and the interaction of the end portion 304 in the indentation 306, the first locking mechanisms 280 and 282 initially may resist release of the first and second catch portions 244 and 246 during contraction of the actuators 284 are contracted.

The actuator mechanism 270 also can include a release and second locking mechanism 320 that can be used in overcoming such initial resistance of the first locking mechanisms 280 and 282. As depicted in FIG. 8B, the mechanism 320 includes a collar portion 322, a pin 324, a first actuator 326, and a second actuator 328. The collar portion 322 is attached to the housing 260 by the pin 324, the first actuator 326 is attached to the collar portion 322 via a pinned connection 330 and attached to the first catch portion 244 via a pinned connection 332, and the second actuator 328 is attached to the collar portion 322 via a pinned connection 334 and attached to the second catch portion 246 via a pinned connection 336. Respective actuation of the first and second actuators 326 and 328 serves to pivot the first and second catch portions 244 and 246 away from the engaged second positions thereof. In doing so, the first and second actuators 326 and 328 push the contact surfaces 312 against the contact surfaces 310 to correspondingly force the end portion 304 out of the indentation 306. Thereafter, the actuators 284 can be contracted to move the contact surfaces 310 away from the contact surfaces 312, and release the first and second catch portions 244 and 246. Thereafter, the actuator 272 can be contracted to pivot the first and second catch portions 244 and 246 toward the disengaged first position.

To increase the pressure of the first and second catch portions 244 and 246 on the first and second lip portions 230 and 232 and/or the first and second sidewall portions 254 and 256, respectively, and further secure attachment of the complimentary engagement portion 240 to first end portion 110, the collar portion 322 can be rotated via rotation of the pin 324. Rotation of the collar portion 322 (clockwise rotation in FIG. 8B) serves to pull on the first actuator 326 and the second actuator 328 which in turns pulls on the first and second catch portions 244 and 246 to further increase pressure of the first and second catch portions 244 and 246 on the first and second lip portions 230 and 232 and/or the first and second sidewall portions 254 and 256, respectively. As such, the actuation of the mechanism 320 can serve maintaining the interconnection of the surgical platform portion 12 to the robotic system R or the sub-system. Rotation of the collar portion 322 (counterclockwise rotation in FIG. 8B) can be used in releasing the first and second catch portions 244 and 246 to afford movement thereof from the engaged second position to the disengaged first position.

Figure 11:
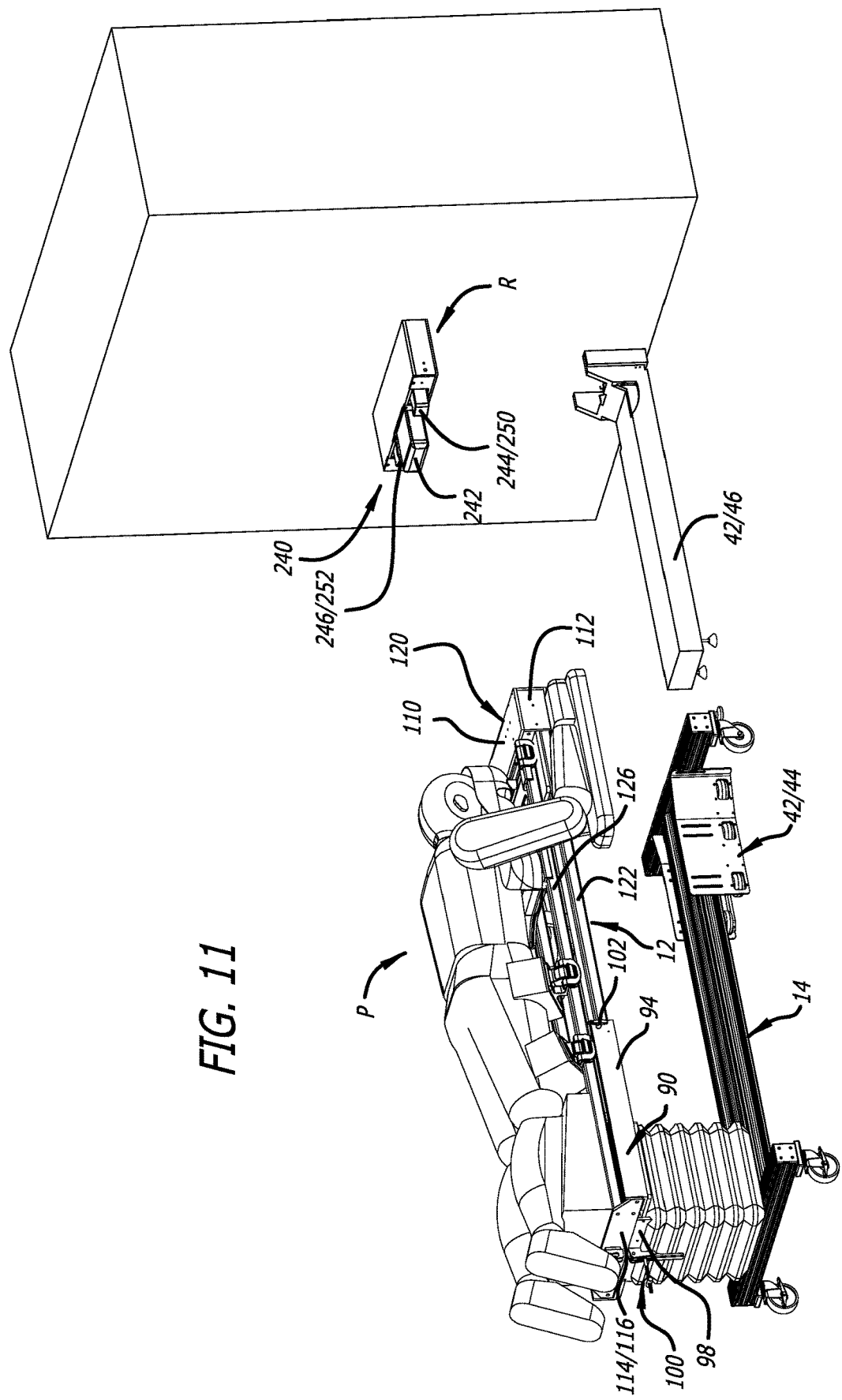
FIG. 11 is a side, perspective view of the surgical platform and trolley assembly of FIG. 1 with the patient positioned thereon being wheeled into position adjacent to the representation of the surgical robotic system or robotic surgical guidance system.
Figure 12:
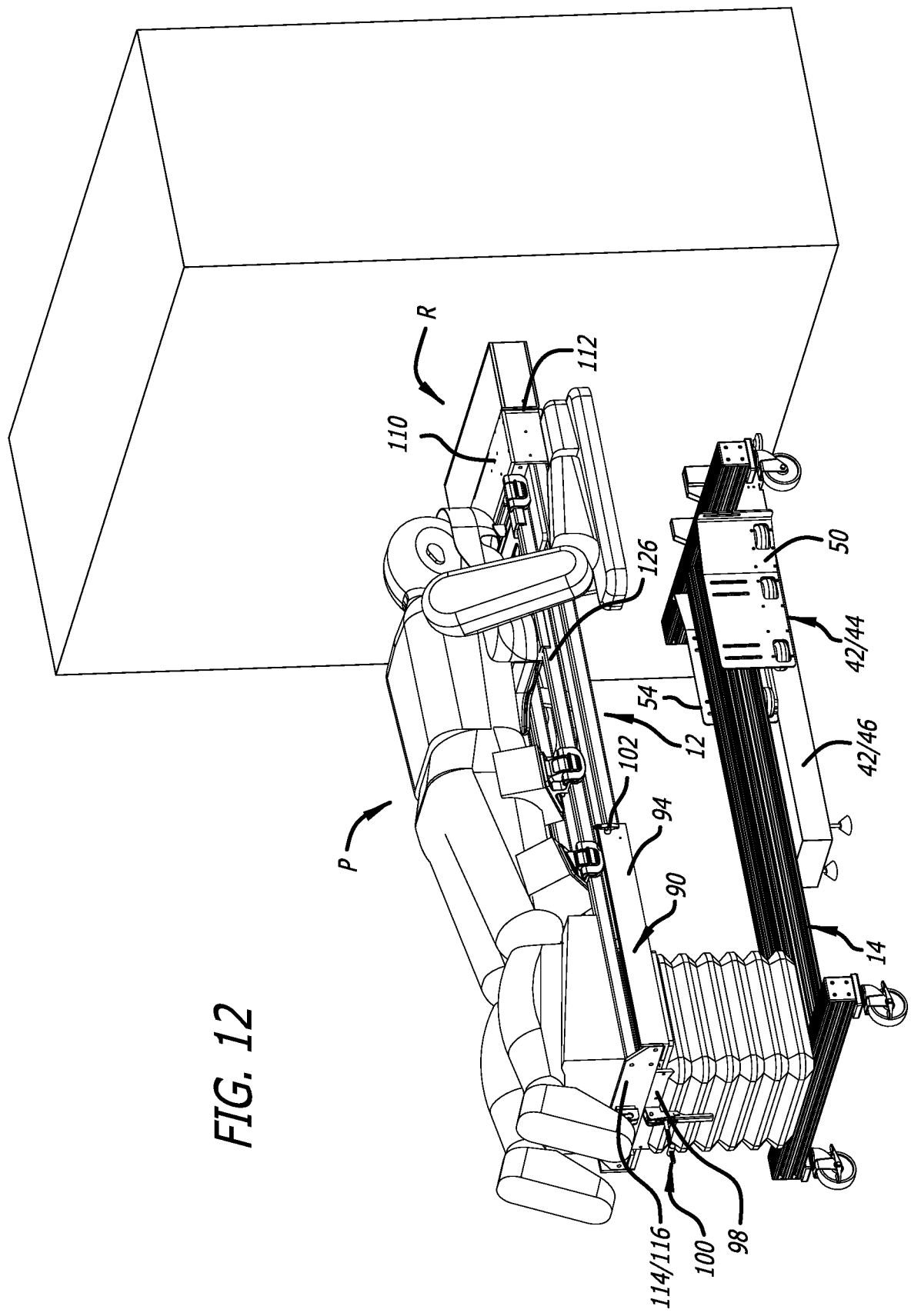
FIG. 12 is a side, perspective view of the trolley portion of the surgical platform and trolley assembly of FIG. 1 positioned relative to the surgical robotic system or robotic surgical guidance system via engagement of the respective portions of the positioner, of the platform portion of the surgical platform and trolley assembly of FIG. 1 with the patient positioned thereon attached relative to the surgical robotic system or robotic surgical guidance system, and of the surgical platform connected to the trolley portion.

During use thereof, the platform and trolley assembly 10, as depicted in FIG. 11, is wheeled relative to the robotic system R. Thereafter, as depicted in FIG. 12, the tongue portion 46 is inserted between the first plate portion 50 and the second plate portion 54, under the first end member 22 and the cross member(s) 30, and into the receiving area $A_1$ of the receiver portion 44. In doing so, the first lateral side surface 70 of the tongue portion 46 contacts the bumper wheels 62 rotatably mounted to the first plate portion 50, and the second lateral side surface 72 of the tongue portion 46 contacts the bumper wheels 62 rotatably mounted to the second plate portion 54 to initially position the surgical platform and trolley assembly 10 relative to the robotic system R.

Figure 13:
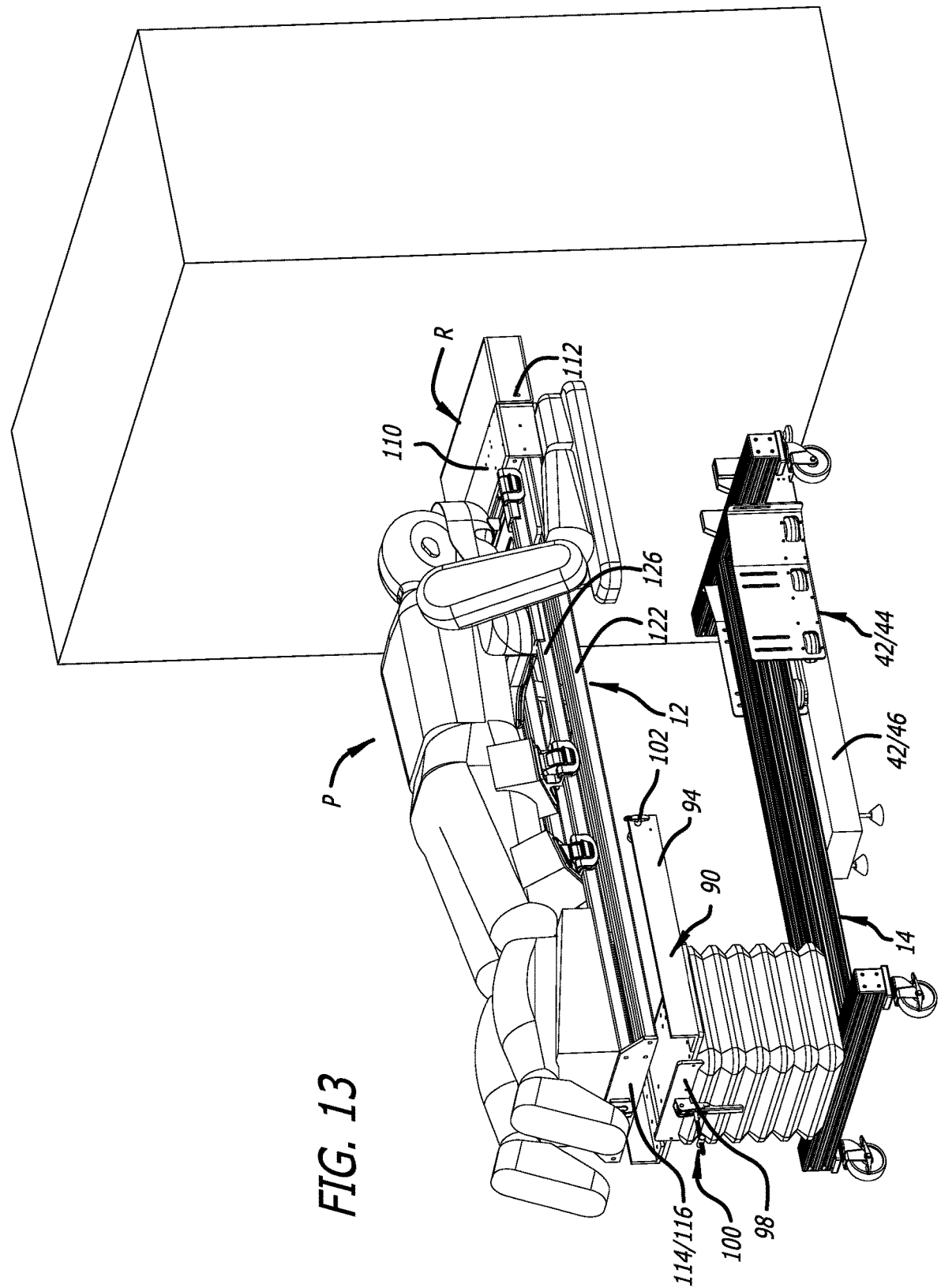
FIG. 13 is a side, perspective view of the trolley portion of the surgical platform and trolley assembly of FIG. 1 positioned relative to the surgical robotic system or robotic surgical guidance system via engagement of the respective portions of the positioner, of the platform portion of the surgical platform and trolley assembly of FIG. 1 with the patient positioned thereon attached relative to the surgical robotic system or robotic surgical guidance system, of the surgical platform disconnected from the trolley portion, and of a lifting/adjustment portion of the trolley portion being in a lowered position.
Figure 14:
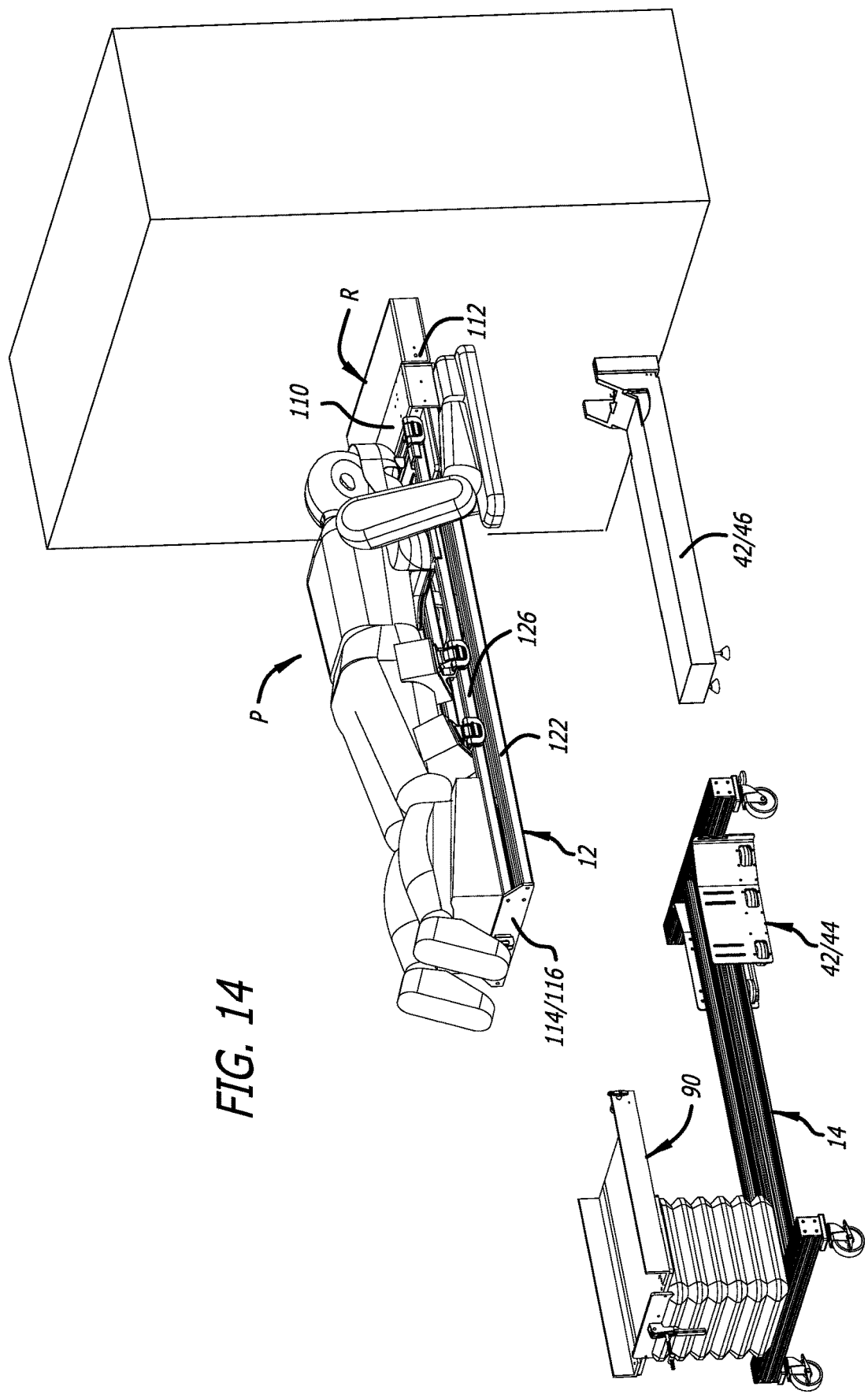
FIG. 14 is a side, perspective view of the platform portion of the surgical platform and trolley assembly of FIG. 1 with the patient positioned thereon attached relative to the surgical robotic system or robotic surgical guidance system, of the lifting/adjustment portion of the trolley portion of the surgical platform and trolley assembly of FIG. 1 being in the lowered position, and of the trolley portion being wheeled away.
Figure 15:
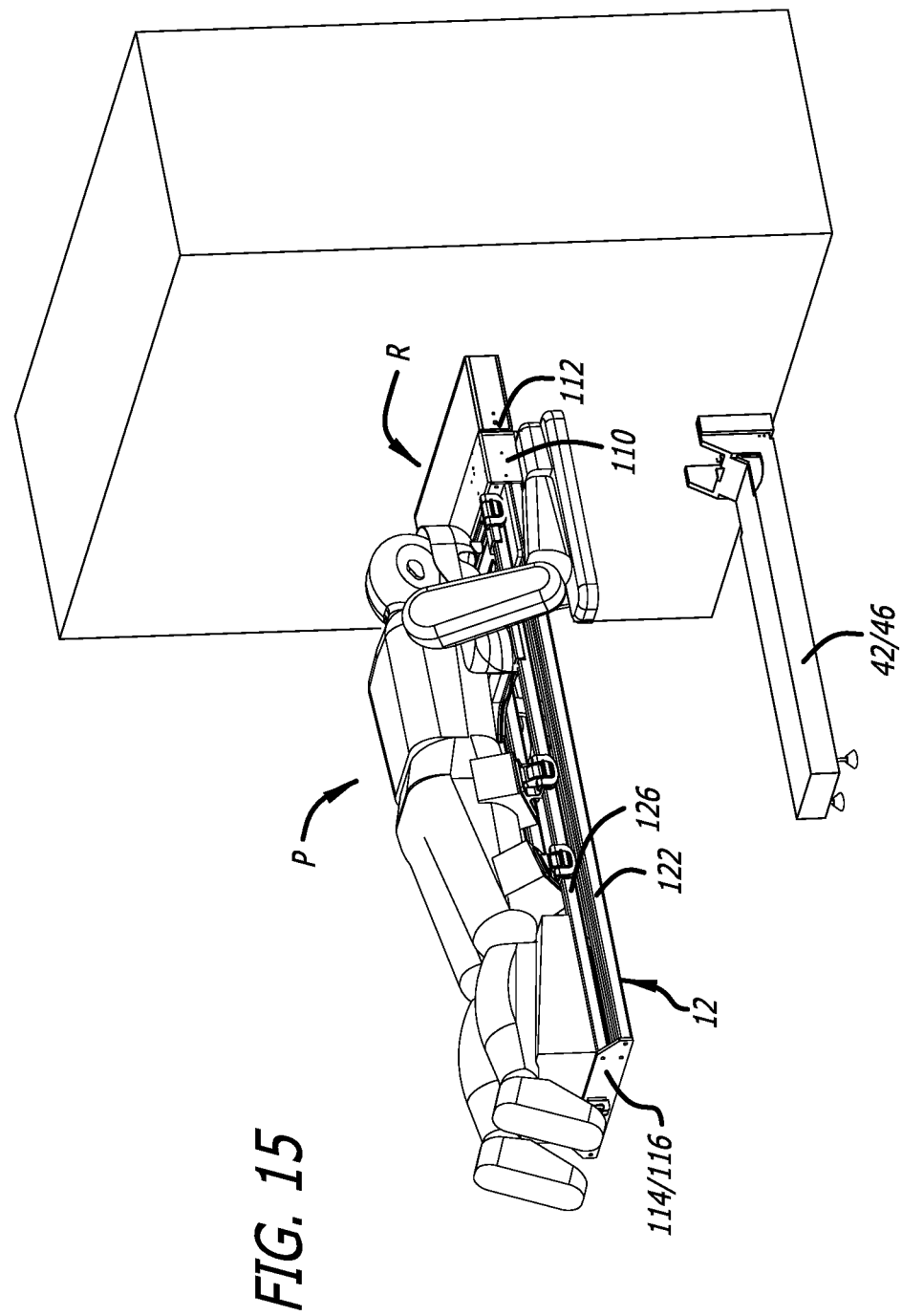
FIG. 15 is a side, perspective view of the platform portion of the surgical platform and trolley assembly of FIG. 1 with the patient positioned thereon being attached relative to the surgical robotic system or robotic surgical guidance system.

After receipt of the tongue portion 46 in the receiving area $A_1$, the engagement portion 120, as depicted in FIG. 13, can be engaged to the complimentary engagement portion 240 via receipt of the tongue portion 242 in the primary opening 222, receipt and engagement of the first catch portion 244 in the first secondary opening 224, receipt and engagement of the second catch portion 246 in the second secondary opening 226, and the respective engagement of the first hook portion 250 and the second hook portion 252 with the first and second lip portions 230 and 232 and/or the first and second sidewall portions 254 and 256 to interconnect the surgical platform portion 12 with the robotic system R. After engagement of the engagement portion 120 and the complimentary engagement portion 240, the surgical platform portion 12 can be detached from the cradle portion 90 via disengagement of the latch mechanism 100 and removal for the pins 102 and 104 from portions of the surgical platform portion 12.

The robotic system R or the sub-system thereafter can be used to lift the surgical platform portion 12 away from the trolley portion 14 (FIG. 14), and the trolley portion 14 can be wheeled away from the surgical platform portion 12 (FIG. 15) until use of the robotic system R is complete. As such, the surgical platform portion 12 is cantilevered relative to the robotic system or the sub-system to provide space under portions of the surgical platform portion 12, and such space, for example, can be used to facilitate use of an O-arm, a C-arm, and/or other electromagnetic imaging device for electromagnetic imaging of the patient P. The robotic system R or the sub-system can then orient and reorient the patient P for surgery by raising or lowering the surgical platform portion 12, tilting the surgical platform portion 12 forward and backward to change its angle in a vertical plane aligned with the mid-longitudinal axis L3, and tilting the surgical platform portion 12 side-to-side to change its angle in a vertical plane perpendicular to the mid-longitudinal axis L3.

With the surgical platform portion 12 and the patient P properly positioned, the robotic system R or the sub-system then can be used for performing surgery or facilitating performance of surgery on the patient P. The surgical platform portion 12, the trolley portion 14, the robotic system R, and/or the sub-system can include one or more controllers for controlling the actuators included in the surgical platform portion 12, the trolley portion 14, the robotic system R, and/or the sub-system to facilitate the operation thereof and/or to coordinate movement therebetween. When the surgery is complete, the trolley portion 14 can be used again to facilitate disconnection of the surgical platform portion 12 from the robotic system R or the sub-system in the reverse order of the interconnection described above.

Figure 16:
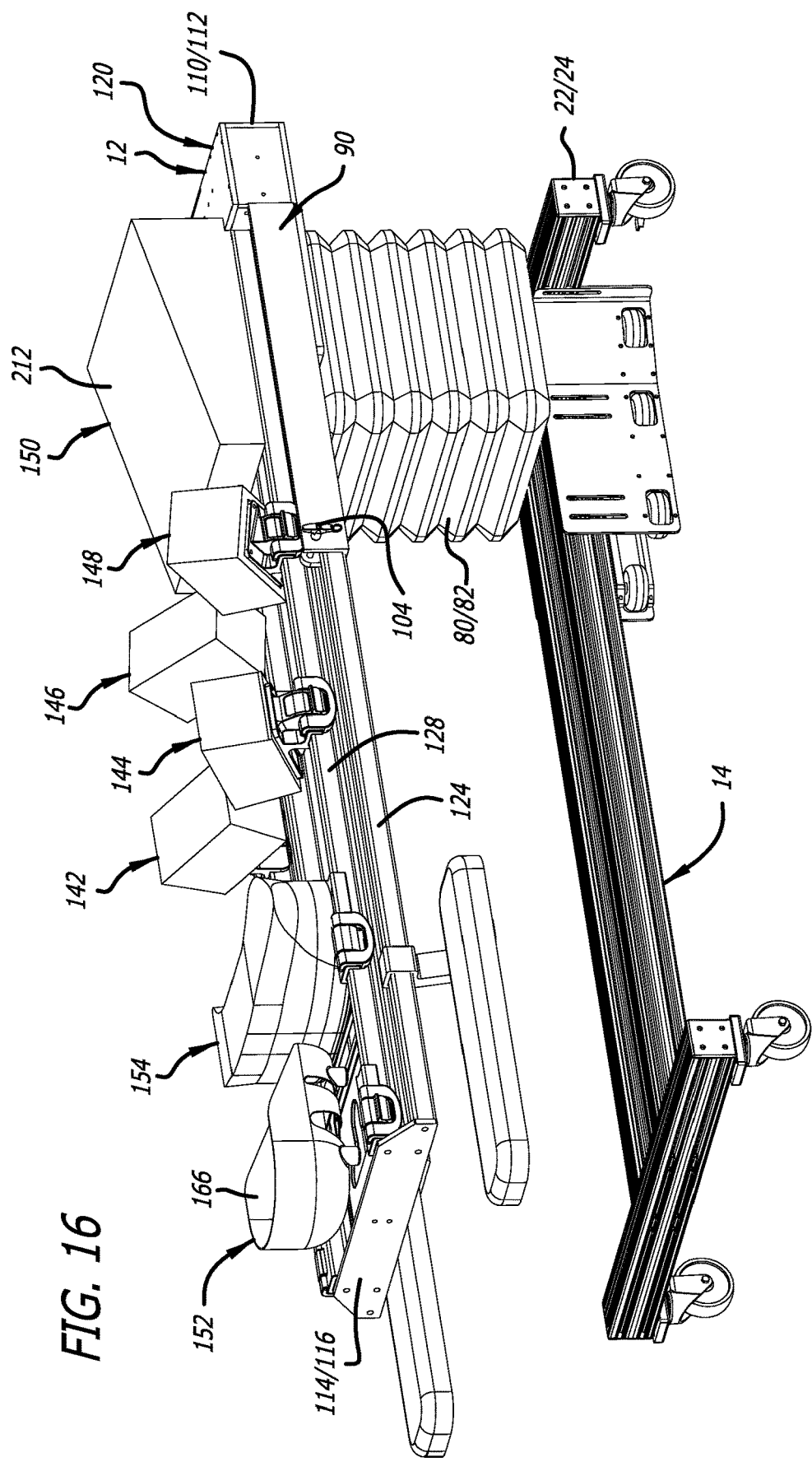
FIG. 16 is a side, perspective view of a modified surgical platform and trolley assembly such that patient support portions are reversed in direction on a platform portion thereof in comparison to the surgical platform and trolley assembly of FIG. 1.
Figure 17:
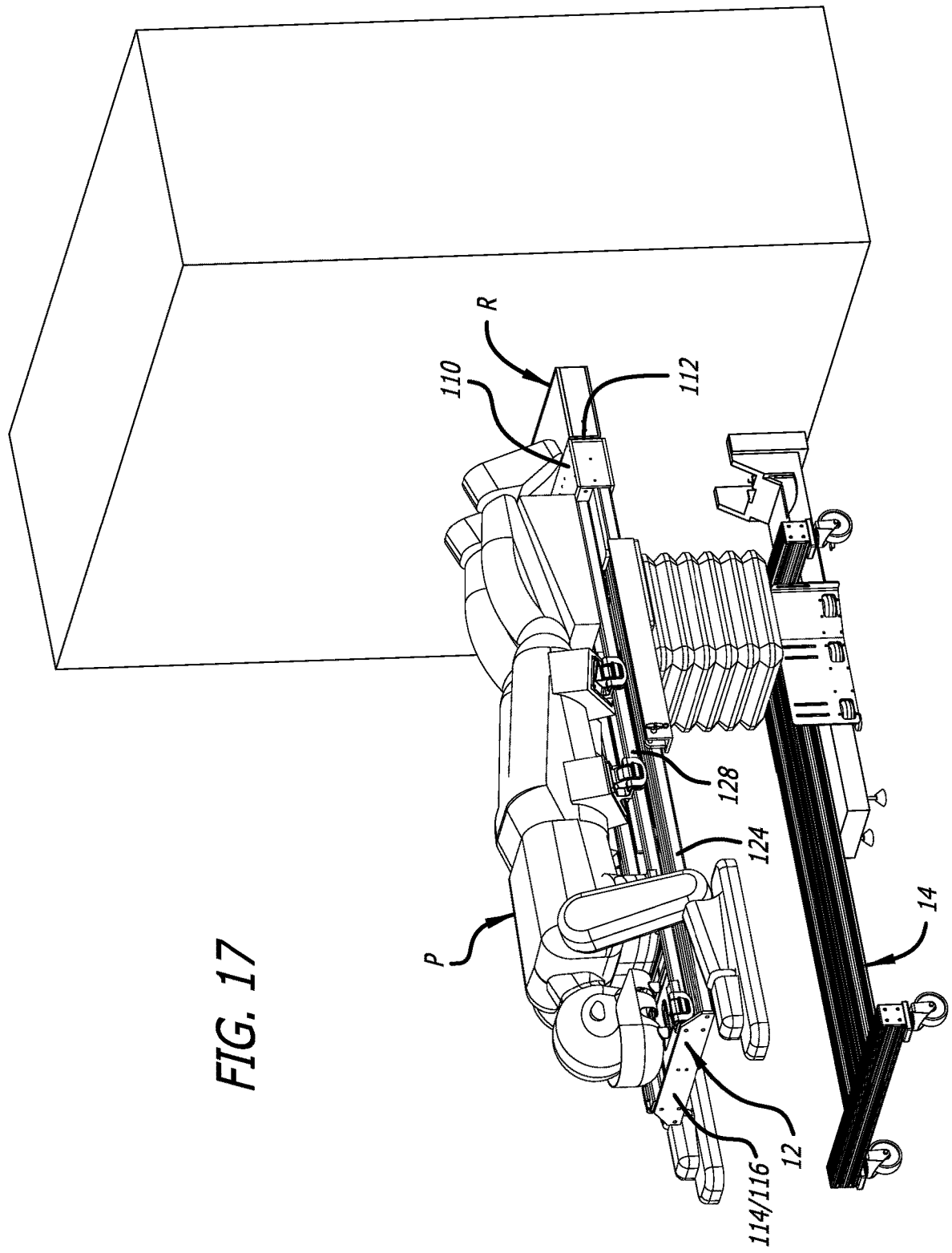
FIG. 17 is a side, perspective view of the platform of the modified surgical platform and trolley assembly of FIG. 16 positioned relative the representation of the surgical robotic system or robotic surgical guidance system.

Additionally, the head and chest support portion 140, the first upper thigh support 142, the second upper thigh support 144, the first lower thigh support 146, the second upper thigh support 148, and/or the lower leg support 150 can be reversed in position along the first inner rail 126 and/or the second inner rail 128 or along the first outer rail 122 and/or the second outer rail 124. As depicted in FIGS. 16 and 17, the patient P can be supported in a reverse direction on the surgical platform portion 12, and the patient P can be oriented in a reverse direction relative to the robotic system R. Furthermore, the position of the lifting/adjustment portion 80 also can be relocated on the support structure 20 of the trolley portion 12 at and adjacent the first end 24 thereof. The reverse position of the various patient support portions and/or the relocation of the lifting/adjustment portion 80 affords positioning of the patient P feet-first relative to the robotic system R. As depicted in FIGS. 16 and 17, the placement of the surgical platform portion 12 relative to the trolley portion 14 can require that the surgical platform portion 12 be attached in different locations to the cradle portion 90.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

We claim:

1. A surgical platform and trolley assembly and an interface of a robotic system, comprising:
the surgical platform and trolley assembly comprising:
a trolley portion including a support structure, a lifting/adjustment portion, and a carriage portion, the support structure having a first end, an opposite second end, a first end portion at the first end, a second end portion at the second end, and at least one cross member extending between the first end portion and the second end portion,
the lifting/adjustment portion having a height that can be expanded and contracted relative to the support structure between a fully-contracted position and a fully-expanded position, and the lifting/adjustment portion being supported by the support structure at and adjacent the second end thereof, and
the carriage portion including at least one of a first side portion, a second side portion, and an end portion, and a first portion of a connector attached to or received in the at least one of the first side portion, the second side portion, and the end portion, the carriage portion being supported by the lifting/adjustment portion, and being moveable upwardly relative to the support structure via expansion of the lifting/adjustment portion and downwardly relative to the support structure via contraction of the lifting/adjustment portion, and
a surgical platform portion including a first end, an opposite second end, a first end portion at the first end, a second end portion at the second end, at least a first rail and a second rail extending between the first end portion and the second end portion, a head support, a chest support, and at least a first thigh support and a second thigh support supported between the at least a first rail and a second rail, and a second portion of the connector attached to or received in at least one of the second end portion and the at least a first rail and a second rail, the surgical platform portion being supportable at and adjacent the second end thereof by the lifting/adjustment portion, and connectable relative to the carriage portion via engagement of the first and second portions of the connector, the first end portion including a primary aperture and at least one secondary aperture provided to receive portions of the interface of the robotic system; and
the interface of the robotic system comprising a tongue portion and at least one catch portion, the tongue portion being receivable in the primary aperture, and the at least one catch portion being receivable in the at least one secondary aperture to interconnect the surgical platform portion relative to the robotic system;
wherein, when the surgical platform portion is supported by and connected to the carriage portion, the trolley portion can be positioned and repositioned relative to the robotic system to position the first end portion of the surgical platform portion adjacent the interface of the robotic system so that the tongue portion is received in the primary aperture and the at least one catch portion is received in the at least one secondary aperture to interconnect the surgical platform portion relative to the robotic system; and
wherein, when the surgical platform portion is interconnected relative to the robotic system, the surgical platform portion can be disconnected from the carriage portion via disengagement of the first and second portions of the connector, and the trolley portion can be removed from adjacent the robotic system.

2. The surgical platform and trolley assembly and the interface of claim 1, wherein the lifting/adjustment portion is configured to tip the first end of the surgical platform portion upwardly and downwardly relative to the support structure, and configured to tilt the surgical platform portion side-to-side relative to the support structure.

3. The surgical platform and trolley assembly and the interface of claim 1, further comprising a first positioner portion attached to the trolley portion and a second positioner portion attached relative to the robotic system, and engagement of the first positioner portion and the second positioner portion initially positions the surgical platform and trolley assembly relative to the robotic system.

4. The surgical platform and trolley assembly and the interface of claim 3, wherein the first positioner portion includes a first plate portion and a second plate portion spaced apart from one another, and defines with an undersurface of the support structure a cavity, and the second positioner portion includes a tongue portion extending outwardly from the robotic system, the tongue portion being receivable within the cavity to position the trolley portion relative to the robotic system.

5. The surgical platform and trolley assembly and the interface of claim 3, wherein at least one controller is provided in at least one of the surgical platform and trolley assembly and the robotic system, the controller, after engagement of the first positioner portion and the second positioner portion, controlling operation of the lifting/adjustment portion to position the first end portion of the surgical platform portion adjacent the interface of the robotic system.

6. The surgical platform and trolley assembly and the interface of claim 1, wherein the at least one secondary aperture includes a first secondary aperture provided on a first side of the primary aperture and a second secondary aperture provided on a second side of the primary aperture, and the at least one catch portion includes a first catch portion provided on a first side of the tongue portion and a second catch portion provided on a second side of the tongue portion, the first catch portion being receivable in the first secondary aperture and the second catch portion being receivable in the second secondary aperture.

7. The surgical platform and trolley assembly and the interface of claim 6, wherein the first catch portion and the second catch portion are each actuatable between a disengaged first position and an engaged second position, and wherein, when the first catch portion and the second catch portion are in the disengaged first position, the first catch portion and the second catch portion are insertable into the first secondary aperture and the second secondary aperture, respectively, and, when the first catch portion and the second catch portion are in the engaged position, the first catch portion and the second catch portion are each contactable with portions of the first end portion adjacent the first secondary aperture and the second secondary aperture, respectively, to interconnect the interface with the surgical platform portion.

8. The surgical platform and trolley assembly and the interface of claim 7, wherein the first catch portion and the second catch portion each include a proximal end and a hook portion provided at a distal end, and the first secondary aperture and the secondary aperture each include a lip portion, and wherein, when the first catch portion and the second catch portion are received in the first secondary aperture and the second secondary aperture, respectively, and in the engaged second position, the hook portions are engageable to the lip portions to maintain engagement between the interface and surgical platform portion.

9. A surgical platform and trolley assembly and an interface of a robotic system, comprising:
the surgical platform and trolley assembly comprising:
a trolley portion including a support structure, and a carriage portion supporting a surgical platform above the support structure, the carriage portion including at least one of a first side portion, a second side portion, and an end portion, and a first portion of a connector attached to or received in the at least one of the first side portion, the second side portion, and the end portion, and
a surgical platform portion including a first end, an opposite second end, a first end portion at the first end, a second end portion at the second end, at least a first rail and a second rail extending between the first end portion and the second end portion, a head support, a chest support, and at least a first thigh support and a second thigh support supported between the at least a first rail and a second rail, and a second portion of the connector attached to or received in at least one of the second end portion and the at least a first rail and a second rail, the surgical platform portion connectable relative to the carriage portion via engagement of the first and second portions of the connector, the first end portion including a primary aperture and at least one secondary aperture provided to receive portions of the interface of the robotic system; and
the interface of the robotic system comprising a tongue portion and at least one catch portion, the tongue portion being receivable in the primary aperture, and the at least one catch portion being receivable in the at least one secondary aperture to interconnect the surgical platform portion relative to the robotic system;
wherein, when the surgical platform portion is supported by and connected to the carriage portion, the trolley portion can be positioned and repositioned relative to the robotic system to position the first end portion of the surgical platform portion adjacent the interface of the robotic system so that the tongue portion is received in the primary aperture and the at least one catch portion is received in the at least one secondary aperture to interconnect the surgical platform portion relative to the robotic system; and
wherein, when the surgical platform portion is interconnected relative to the robotic system, the surgical platform portion can be disconnected from the carriage portion via disengagement of the first and second portions of the connector, and the trolley portion can be removed from adjacent the robotic system.

10. The surgical platform and trolley assembly and the interface of claim 9, further comprising a first positioner portion attached to the trolley portion and a second positioner portion attached relative to the robotic system, the first positioner portion including a first plate portion and a second plate portion spaced apart from one another, and defining with an undersurface of the support structure a cavity, and the second positioner portion including a tongue portion extending outwardly from the robotic system, the tongue portion being receivable within the cavity to position the trolley portion relative to the robotic system.

11. The surgical platform and trolley assembly and the interface of claim 9, wherein the at least one secondary aperture includes a first secondary aperture provided on a first side of the primary aperture and a second secondary aperture provided on a second side of the primary aperture, and the at least one catch portion includes a first catch portion provided on a first side of the tongue portion and a second catch portion provided on a second side of the tongue portion, the first catch portion being receivable in the first secondary aperture and the second catch portion being receivable in the second secondary aperture.

12. The surgical platform and trolley assembly and the interface of claim 11, wherein the first catch portion and the second catch portion are each actuatable between a disengaged first position and an engaged second position, and wherein, when the first catch portion and the second catch portion are in the disengaged first position, the first catch portion and the second catch portion are insertable into the first secondary aperture and the second secondary aperture, respectively, and, when the first catch portion and the second catch portion are in the engaged position, the first catch portion and the second catch portion are each contactable with portions of the first end portion adjacent the first secondary aperture and the second secondary aperture, respectively, to interconnect the interface with the surgical platform portion.

13. The surgical platform and trolley assembly and the interface of claim 12, wherein the first catch portion and the second catch portion each include a proximal end and a hook portion provided at a distal end, and the first secondary aperture and the secondary aperture each include a lip portion, and wherein, when the first catch portion and the second catch portion are received in the first secondary aperture and the second secondary aperture, respectively, and in the engaged second position, the hook portions are engageable to the lip portions to maintain engagement between the interface and surgical platform portion.

14. A surgical platform and trolley assembly and an interface of a robotic system, comprising:
the surgical platform and trolley assembly comprising:
a trolley portion including a support structure, a lifting/adjustment portion, and a carriage portion, the support structure having a first end, an opposite second end, a first end portion at the first end, a second end portion at the second end, and at least one cross member extending between the first end portion and the second end portion,
the lifting/adjustment portion having a height that can be expanded and contracted relative to the support structure between a fully-contracted position and a fully-expanded position, and the lifting/adjustment portion being supported by the support structure at and adjacent the second end thereof, and
the carriage portion including at least one of a first side portion, a second side portion, and an end portion, and a first portion of a connector attached to or received in the at least one of the first side portion, the second side portion, and the end portion, and being moveable upwardly via expansion of the lifting/adjustment portion and downwardly relative to the support structure via contraction of the lifting/adjustment portion, and the carriage portion being supported by the lifting/adjustment portion,
a surgical platform portion including a first end, an opposite second end, a first end portion at the first end, a second end portion at the second end, at least a first rail and a second rail extending between the first end portion and the second end portion, a head support, a chest support, and at least a first thigh support and a second thigh support supported between the at least a first rail and a second rail, and a second portion of the connector attached to or received in at least one of the second end portion and the at least a first rail and a second rail, the surgical platform portion being supportable at and adjacent the second end thereof by the lifting/adjustment portion, and connectable relative to the carriage portion via engagement of the first and second portions of the connector, the first end portion including a primary aperture and at least one secondary aperture provided to receive portions of the interface of the robotic system; and at least one controller provided controlling operation of at least portions of the surgical platform and trolley assembly and the robotic system, the controller being configured to control operation of the lifting/adjustment portion to position the first end portion of the surgical platform portion adjacent the interface of the robotic system; and the interface of the robotic system comprising a tongue portion and at least one catch portion, the tongue portion being receivable in the primary aperture, and the at least one catch portion being receivable in the at least one secondary aperture to interconnect the surgical platform portion relative to the robotic system;

wherein, when the surgical platform portion is supported by and connected to the carriage portion, the trolley portion can be positioned and repositioned relative to the robotic system to position the first end portion of the surgical platform portion adjacent the interface of the robotic system so that the tongue portion is received in the primary aperture and the at least one catch portion is received in the at least one secondary aperture to interconnect the surgical platform portion relative to the robotic system; and wherein, when the surgical platform portion is interconnected relative to the robotic system, the surgical platform portion can be disconnected from the carriage portion via disengagement of the first and second portions of the connector, and the trolley portion can be removed from adjacent the robotic system.

15. The surgical platform and trolley assembly and the interface of claim 14, wherein the lifting/adjustment portion is configured to tip the first end of the surgical platform portion upwardly and downwardly relative to the support structure, and configured to tilt the surgical platform portion side-to-side relative to the support structure.

16. The surgical platform and trolley assembly and the interface of claim 14, further comprising a first positioner portion attached to the trolley portion and a second positioner portion attached relative to the robotic system, and engagement of the first positioner portion and the second positioner portion initially positions the surgical platform and trolley assembly relative to the robotic system.

17. The surgical platform and trolley assembly and the interface of claim 16, wherein the first positioner portion includes a first plate portion and a second plate portion spaced apart from one another, and defines with an undersurface of the support structure a cavity, and the second positioner portion includes a tongue portion extending outwardly from the robotic system, the tongue portion being receivable within the cavity to position the trolley portion relative to the robotic system.

18. The surgical platform and trolley assembly and the interface of claim 16, wherein the at least one controller is provided in at least one of the surgical platform and trolley assembly and the robotic system, the controller, after engagement of the first positioner portion and the second positioner portion, controlling operation of the lifting/adjustment portion to position the first end portion of the surgical platform portion adjacent the interface of the robotic system.

19. The surgical platform and trolley assembly and the interface of claim 14, wherein the at least one secondary aperture includes a first secondary aperture provided on a first side of the primary aperture and a second secondary aperture provided on a second side of the primary aperture, and the at least one catch portion includes a first catch portion provided on a first side of the tongue portion and a second catch portion provided on a second side of the tongue portion, the first catch portion being receivable in the first secondary aperture and the second catch portion being receivable in the second secondary aperture.

20. The surgical platform and trolley assembly and the interface of claim 19, wherein the first catch portion and the second catch portion are each actuatable between a disengaged first position and an engaged second position, and wherein, when the first catch portion and the second catch portion are in the disengaged first position, the first catch portion and the second catch portion are insertable into the first secondary aperture and the second secondary aperture, respectively, and, when the first catch portion and the second catch portion are in the engaged position, the first catch portion and the second catch portion are each contactable with portions of the first end portion adjacent the first secondary aperture and the second secondary aperture, respectively, to interconnect the interface with the surgical platform portion.

* * * * *